(12) United States Patent
Harder et al.

(10) Patent No.: US 8,735,104 B2
(45) Date of Patent: May 27, 2014

(54) DIRECT NUCLEIC ACID ANALYSIS

(75) Inventors: Chris Harder, Nepean (CA); Kelly Jackson, Ottawa (CA); Samantha Prevost, Ottawa (CA); Hannah Bernatchez, Ottawa (CA); Paul Lem, Ottawa (CA); Martin Cloake, Ottawa (CA); Ningke Kuang, Ottawa (CA); Colin Davis, Ottawa (CA)

(73) Assignee: Spartan Bioscience Inc., Ottawa, Ontario (CA)

( * ) Notice: Subject to any disclaimer, the term of this patent is extended or adjusted under 35 U.S.C. 154(b) by 0 days.

(21) Appl. No.: 13/637,006

(22) PCT Filed: Mar. 31, 2011

(86) PCT No.: PCT/IB2011/001176
§ 371 (c)(1),
(2), (4) Date: Nov. 7, 2012

(87) PCT Pub. No.: WO2011/121454
PCT Pub. Date: Oct. 6, 2011

(65) Prior Publication Data
US 2013/0045477 A1 Feb. 21, 2013

Related U.S. Application Data

(60) Provisional application No. 61/319,610, filed on Mar. 31, 2010, provisional application No. 61/357,043, filed on Jun. 21, 2010, provisional application No. 61/414,772, filed on Nov. 17, 2010, provisional application No. 61/414,776, filed on Nov. 17, 2010.

(51) Int. Cl.
*C12P 19/34* (2006.01)
(52) U.S. Cl.
USPC .................................................... 435/91.2
(58) Field of Classification Search
USPC .................................................... 435/91.2
See application file for complete search history.

(56) References Cited

U.S. PATENT DOCUMENTS

2004/0259226 A1* 12/2004 Robey et al. ............... 435/252.3
2008/0311579 A1 12/2008 French et al.
2011/0111399 A1* 5/2011 O'Hara et al. .................... 435/6

FOREIGN PATENT DOCUMENTS

WO   WO 2004/072230 A2   8/2004
WO   WO 2004/105949 A1   12/2004

OTHER PUBLICATIONS

Akada, R. et al., DNA Extraction Method for Screening Yeast Clones by PCR, BioTechniques, 28:668-674 (2000).
Ausubel, F. et al., Short Protocols in Molecular Biology, Third Edition, John Wiley & Sons (1995).
French, D.J. et al., Ultra-rapid DNA analysis using HyBeacon™ probes and direct PCR amplification from saliva, Molecular and Cellular Probes, 16(5):319-326 (2002).
Garcia-Closas, M. et al., Collection of Genomic DNA from Adults in Epidemiological Studies by Buccal Cytobrush and Mouthwash. Cancer Epidemiology, Biomarkers & Prevention, 10(6): 687-696. (2001).
Hafner, G.J. et al., Isothermal Amplification and Multimerization of DNA by *Bst* DNA Polymerase, BioTechniques, 30:852-867 (2001).
Innis, M.A. et al., PCR Protocols: A Guide to Methods and Applications, Academic Press, Inc. (1990).
International Search Report for PCT/IB2012/002849, 2 pages (Apr. 10, 2013).
Ochert, A.S. et al., Inhibitory Effect of Salivary Fluids on PCR: Potency and Removal, Genome Research, 3:365-368 (1994).
Saiki, R.K., Amplification of Genomic DNA in PCR Protocols: A Guide to Methods and Application, pp:13-20, Academic Press, Inc. (1990).
Sambrook, J. et al., Molecular Cloning: A Laboratory Manual, Second Edition, Cold Spring Harbor Laboratory Press (1989).
Tanabe, S. et al., A Real-Time Quantitative PCR Detection Method for Pork, Chicken, Beef, Mutton, and Horseflesh in Foods, Bioscience, Biotechnology, and Biochemistry, 71(12): 3131-3135 (2007).
Weyant, R.S. et al., Effect of Ionic and Nonionic Detergents on the *Taq* Polymerase, BioTechniques, 9:308-309 (1990).
Wharam, S.D. et al., Specific detection of DNA and RNA targets using a novel isothermal nucleic acid amplification assay based on the formulation of a three-way junction structure, Nucleic Acid Research, 29 (11):e54 (2001).
Whelen, A.C. et al., Direct Genotypic Detection of *Mycobacterium tuberculosis Rifampin* Resistance in Clinical Specimens by Using Single-Tube Heminested PCR, Journal of Clinical Microbiology, 33(3):556-561 (1995).
Written Opinion for PCT/IB2012/002849, 4 pages (Apr. 10, 2013).
International Search Report for PCT/IB2011/001176, mailed on Jan. 4, 2012 (5 pages).
Written Opinion for PCT/IB2011/001176, mailed on Jan. 4, 2012 (5 pages).
Saiki, R.K. et al., "The Design and Optimization of the PCR". PCR Technology, pp. 7-16, 1989.
Spangler, R. et al., "Optimizing Taq Polymerase Concentration for Improved Signal-to-Noise in the Broad Range Detection of Low Abundance Bacteria". PloS ONE, Public Library of Science, 4:9:1-10, 2009.

* cited by examiner

*Primary Examiner* — Cynthia B Wilder
(74) *Attorney, Agent, or Firm* — Choate, Hall & Stewart LLP; Brenda Herschbach Jarrell; Charles Lyon

(57) ABSTRACT

Methods and apparatus are described for nucleic acid analysis of swab samples without the need for purification.

46 Claims, 9 Drawing Sheets

*Data are shown as average ± SD*

*Data are shown as average ± SD*

*Data are shown as average ± SD*

*Data are shown as average ± SD*

*Data are shown as average ± SD*

*Data are shown as average ± SD*

… (1)

```
                              SEQUENCE LISTING

<160> NUMBER OF SEQ ID NOS: 8

<210> SEQ ID NO 1
<211> LENGTH: 25
<212> TYPE: DNA
<213> ORGANISM: Homo sapiens

<400> SEQUENCE: 1
tgcaataatt tcccactat cattg                                           25

<210> SEQ ID NO 2
<211> LENGTH: 26
<212> TYPE: DNA
<213> ORGANISM: Homo sapiens

<400> SEQUENCE: 2
ccaaaatatc actttccata aaagca                                         26

<210> SEQ ID NO 3
<211> LENGTH: 25
<212> TYPE: DNA
<213> ORGANISM: Homo sapiens

<400> SEQUENCE: 3
cgcagatttc ccgggaaccc ctgcg                                          25

<210> SEQ ID NO 4
<211> LENGTH: 27
<212> TYPE: DNA
<213> ORGANISM: Homo sapiens

<400> SEQUENCE: 4
cgcagttatt tcccaggaac ccctgcg                                        27

<210> SEQ ID NO 5
<211> LENGTH: 22
<212> TYPE: DNA
<213> ORGANISM: Sus scrofa

<400> SEQUENCE: 5
gttgcaaatc ctaacaggcc tg                                             22

<210> SEQ ID NO 6
<211> LENGTH: 25
<212> TYPE: DNA
<213> ORGANISM: Sus scrofa

<400> SEQUENCE: 6
cgtttgcatg tagatagcga ataac                                          25

<210> SEQ ID NO 7
<211> LENGTH: 16
<212> TYPE: DNA
<213> ORGANISM: Homo sapiens

<400> SEQUENCE: 7
ttatttcccg ggaacc                                                    16

<210> SEQ ID NO 8
<211> LENGTH: 16
```

```
<212> TYPE: DNA
<213> ORGANISM: Homo sapiens

<400> SEQUENCE: 8
ttatttccca ggaacc                                                    16
```

DIRECT NUCLEIC ACID ANALYSIS

CROSS REFERENCE TO RELATED APPLICATIONS

This application is a National Phase application under 35 U.S.C. §371 of International Application No. PCT/IB2011/001176, filed Mar. 31, 2011; which claims priority to U.S. provisional patent application 61/319,610, filed Mar. 31, 2010; U.S. provisional patent application 61/357,043, filed Jun. 21, 2010; U.S. provisional patent application 61/414,776, filed Nov. 17, 2010; and U.S. provisional application 61/414,772, filed Nov. 17, 2010; all of which are hereby incorporated by reference herein in their entireties.

TECHNICAL FIELD OF THE INVENTION

The invention relates to the field of diagnostic assays, in particular, nucleic acid amplification-based assays.

BACKGROUND

Nucleic acids are used frequently in the clinical setting to identify genetic mutations and to diagnose bacterial and/or viral infections. Such methods generally require use of nucleic acids isolated or extracted from biological samples.

A commonly used method for isolating DNA from a biological sample (e.g., blood or saliva) involves lysing the cells contained in the sample with a combination of a proteolytic enzyme and a detergent followed by extracting the mixture with an organic solvent, e.g., phenol and chloroform, so that the DNA enters the aqueous phase and the protein enters the organic phase. The DNA in the aqueous phase is then concentrated by alcohol precipitation and re-suspended in a suitable volume for analysis. Such methods are, however, time-consuming and generally require the use of toxic reagents.

Simpler methods using fewer reagents have been reported. For example, DNAZOL Direct (Molecular Research Center, Inc.) is an alkaline solution containing polyethylene glycol and other additives. Buccal swabs and whole saliva samples are incubated in DNAZOL Direct for 15 min. The resulting lysate may be added directly to a polymerase chain reaction (PCR) mix, where the lysate should be less than 10% of the PCR mix by volume.

In another example, 0.25 µl to 5 µl of whole saliva or buccal swab sample may be added directly into a 50 µl PCR mixture containing 1× EZWAY Direct PCR Buffer (Koma Biotech). The PCR cycling program should use an initial denaturation of 95° C. for 5 min followed by cycling denaturation steps of 94° C. for 30 sec to 60 sec.

The disadvantages of DNAZOL Direct and EZWAY Direct PCR Buffer are that they require the use of special reagents and specific incubation or denaturation conditions.

Another approach to bypassing the DNA purification step is the use of specially-modified DNA polymerase enzymes that are resistant to inhibitors in samples. For example, the PHUSION Human Specimen Direct PCR Kit (Finnzymes) claims to allow PCR directly from unpurified human samples. A tiny amount of sample is used directly in the PCR reaction with no prior purification steps. Suitable sample materials include buccal swabs, saliva, amniotic fluid, hair, fingernails, teeth, and skin biopsies. The kit is based on modified PHUSION Hot Start II High-Fidelity DNA Polymerase. This specially engineered proofreading DNA polymerase is fast, robust and highly tolerant of many PCR inhibitors present in human tissues. The disadvantage of this approach is that it requires a proprietary DNA polymerase that may be more expensive than standard DNA polymerase.

Simpler methods for analyzing whole saliva samples have been reported. For example, Ochert et al. (1994) boiled whole saliva for 5 min and then used it as the sample for PCR. This method resulted in successful PCR for 7 out of 10 samples. The researchers used 30 µl of boiled sample in a total reaction volume of 50 µl. The PCR cycling program used cycling denaturation steps of 1 min at 94° C. One of the samples, which gave an inconclusive result with 5 min of boiling, generated a positive result after 6 or more minutes of boiling. The researchers concluded that: "[t]he chemical nature of the inhibitors remains to be characterized. By inference, they are unlikely to be proteins because of their relative heat resistance and the observation that extraction procedures based on phenol-chloroform or proteinase K did not prevent inhibition. The persistence of inhibition after processing with gel matrices or ion-exchange resins suggests that low-molecular-weight ionic moieties are also not inhibitors. Polysaccharides are possible candidates." (Ochert AS et al. (1994). Inhibitory effect of salivary fluids on PCR: potency and removal. *Genome Research.* 3: 365-368.)

In another example, French et al. (2002) performed direct PCR amplification from whole saliva using HYBEACON probes on the LIGHTCYCLER instrument. PCR volumes were typically 20 µl A, containing 2 µl of saliva. Saliva samples were diluted to 50% in water. The PCR mixtures used 1 unit of Taq DNA polymerase (Taq from Amersham Pharmacia Biotech or Z-Taq from TaKaRa). The final concentration of PCR primers was 0.5 µM each, and the final concentration of HYBEACON fluorescent probe was 150 nM. The PCR cycling program used an initial denaturation step of 95° C. for 5 min followed by cycling denaturation steps of 95° C. for 0 seconds (i.e., the thermal cycler ramped up to 95 °C. and immediately ramped down to the extension temperature). Saliva samples were typed on the same day that they were collected, although a significant reduction in assay efficiency was not observed with saliva samples stored at 4 ° C. for 2-3 days, or −20° C. The researchers noted that since the number of buccal epithelial cells shed into saliva samples may not be equal from person-to-person and day-to-day, a further study of assay reproducibility and robustness may be required. (French DJ et al. (2002). Ultra-rapid DNA analysis using HYBEACON probes and direct PCR amplification from saliva. *Molecular and Cellular Probes.* 16: 319-326.)

Researchers have found that there is high variability in the concentration of DNA from saliva or buccal swabs in a population of subjects. For example, Garcia-Closas et al. (2001) collected two cytobrush samples each from 40 individuals and found that the amount of human DNA ranged from 0.006 to 13.5 µg after phenol-chloroform DNA purification (Garcia-Closas M et al. (2001). Collection of Genomic DNA from Adults in Epidemiological Studies by Buccal Cytobrush and Mouthwash. *Cancer Epidemiology, Biomarkers & Prevention.* 10(6): 687-696.).

Although boiling whole saliva for 5 minutes or more, or diluting whole saliva and then denaturing at 95° C. for 5 min are relatively simple steps, they still require time and effort on the part of the user. For automated instruments, these steps would require extra mechanical parts and movements to accomplish. In addition, the PCR success rate of 7 out of 10 boiled saliva samples reported by Ochert et al. (1994) makes this method less desirable for clinical applications where higher reliability is typically expected.

SUMMARY OF THE INVENTION

The present disclosure provides methods, systems, and apparatuses for collecting and/or amplifying nucleic acids. In one aspect, the present disclosure provides methods that involve contacting a sample including a nucleic acid with a nucleic acid amplification reagent without purification of nucleic acids from the sample. In some embodiments, the nucleic acid amplification reagent contains at least one of a DNA polymerase at a concentration of at least 1.0 U/reaction, a primer at a concentration of at least 0.2 μM, and a probe of at least 0.2 μM. The sample may, for example, be a swab sample and may be a buccal swab sample. In some embodiments, the DNA polymerase utilized is not specially modified to resist inhibitors. In some embodiments, the DNA polymerase is no more resistant to inhibitors in human samples than is a reference DNA polymerase such as, for example Taq DNA polymerase. In some embodiments, the concentration of DNA polymerase is 2.0 U/reaction or higher.

In some embodiments, the nucleic acid amplification reagents contain primer and probe concentrations higher than typically used in PCR reactions (0.1-0.2 μM). In some embodiments, the primer concentration is greater than 0.2 μM and the probe concentration is greater than 0.2 μM. In some embodiments, the primer concentration is 0.5 μM and the probe concentration is 0.7 μM.

In some embodiments, the nucleic acid amplification reagents contain both DNA polymerase and primer and probe concentrations higher than typically used in PCR reactions.

In some embodiments, the methods further comprise determining whether an amplification product was produced as a result of the nucleic acid amplification reaction.

In some embodiments, the nucleic acid amplification reaction is performed in a reaction vessel and a cap of the reaction vessel is used to collect the buccal sample (e.g., by contacting the cap with the inside cheek or tongue of the subject).

In some embodiments, the cap of the reaction vessel is incorporated into a cap holder device so that the device functions as a buccal swab.

In some embodiments, the nucleic acid amplification reaction is performed within 120 minutes of contacting the buccal sample with the nucleic acid amplification reagents. In some embodiments, the nucleic acid amplification reaction is performed within 60, 30, 15, 10, 5, or 1 minutes of contacting the buccal sample with the nucleic acid amplification reagents.

In some embodiments, the nucleic acid amplification reaction comprises an initial heat denaturation step of 15 minutes or less. In some embodiments, the nucleic acid amplification reaction comprises an initial heat denaturation step of 5 minutes or less, 3 minutes or less, or 1 minute or less.

In some embodiments, the swab sample is collected from a mammal (e.g., a human, dog, cat, cow, sheep, pig, etc.). In some embodiments, the swab sample is collected from an open body cavity. In some embodiments, the swab sample is collected from a body surface. In some embodiments, the swab sample is a buccal sample. In some embodiments, the swab sample is collected from the palm of a hand, inside the folds of the pinna of an ear, an armpit, or inside a nasal cavity.

In some embodiments, the swab sample is collected from a foodstuff. In some embodiments, the foodstuff is raw. In some embodiments, the foodstuff is a fruit, a vegetable, a meat, a fish, or a shellfish. In some embodiments, the meat is pork, beef, chicken, or lamb.

In some embodiments, the nucleic acid amplification reaction is performed in a reaction vessel having a removable cap and the cap is used to collect the swab sample. In some embodiments, a means for holding the cap of the reaction vessel is used when collecting the swab sample. In some embodiments, the cap is contacted with the inside of a cheek or a tongue. In some embodiments, the cap is contacted with the palm of a hand, the inside of the folds of the pinna of an ear, an armpit, or the inside of a nasal cavity. In some embodiments, the cap is contacted with a foodstuff.

In some embodiments, the swab sample is collected from a source and the method is repeated with at least one other swab sample from the same source.

In some embodiments, the swab sample is directly contacted with the nucleic acid amplification reagents without any intervening steps. In some of these embodiments, the nucleic acid amplification reaction is performed in a reaction vessel having a removable cap and the cap is used to collect the swab sample. In some embodiments, the reaction vessel comprises the nucleic acid amplification reagents and the cap is used to seal the reaction vessel after the swab sample has been collected. In some embodiments, a means for holding the cap of the reaction vessel is used when collecting the swab sample.

In some embodiments, the kit further comprises nucleic acid amplification reagents. In some embodiments, the cap is mated with the reaction vessel and the nucleic acid amplification reagents are located within the reaction vessel. In some embodiments, the reaction vessel is empty and the nucleic acid amplification reagents are located within one or more containers that form part of the kit.

In some embodiments, the cap is mated with the reaction vessel.

In some embodiments, the cap is mated with the means for holding the cap.

In some embodiments, the kit further comprises a means for controlling a nucleic acid amplification reaction in the reaction vessel. In some embodiments, the means for controlling a nucleic acid amplification reaction in the reaction vessel comprises a thermal cycler with a well for receiving the reaction vessel.

In some embodiments, the kit further comprises a means for determining whether an amplification product has been produced as a result of the nucleic acid amplification reaction. In some embodiments, the means for determining whether an amplification product has been produced as a result of the nucleic acid amplification reaction comprises a device for measuring fluorescence in the reaction vessel while the reaction vessel is located within the means for controlling a nucleic acid amplification reaction in the reaction vessel.

In another aspect, the methods involve contacting non-buccal samples from human and non-human sources with nucleic acid amplification reagents without purification of nucleic acids in the non-buccal sample and then performing a nucleic acid amplification reaction on a nucleic acid template in the non-buccal sample. In some embodiments, the methods further comprise determining whether an amplification product was produced as a result of the nucleic acid amplification reaction.

BRIEF DESCRIPTION OF THE DRAWINGS

Certain features of a provided closure system are described in detail herein below with reference to the figures, wherein.

DETAILED DESCRIPTION OF CERTAIN EMBODIMENTS

Figure 1:
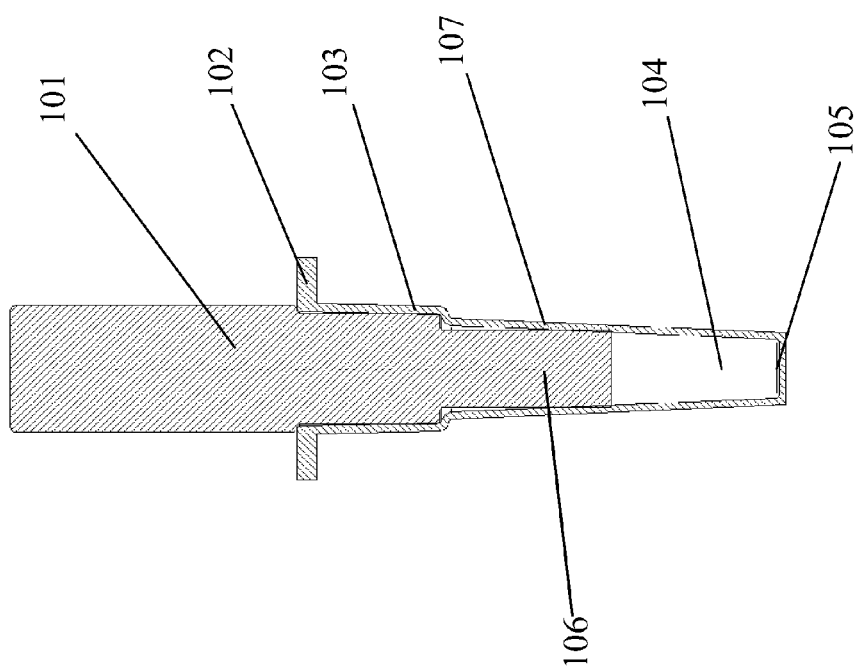
FIG. 1 shows a cross-sectional view of a Spartan DX-12 tube with the cap fully inserted in accordance with embodiments of the present invention.

Definitions. As used herein the following terms shall have the meanings indicated, unless indicated otherwise:

As used herein, the term "about" when used in reference to a numerical value, means plus or minus 10%.

As used herein, the terms "amplification" or "amplify" refer to methods known in the art for copying a target sequence from a template nucleic acid, thereby increasing the number of copies of the target sequence in a sample. Amplification may be exponential or linear. A template nucleic acid may be either DNA or RNA. The target sequences amplified in this manner form an "amplified region" or "amplicon." While the exemplary methods described hereinafter relate to amplification using PCR, numerous other methods are known in the art for amplification of target nucleic acid sequences (e.g., isothermal methods, rolling circle methods, etc.). The skilled artisan will understand that these other methods may be used either in place of, or together with, PCR methods. See, e.g., Saiki, "Amplification of Genomic DNA" in *PCR Protocols*, Innis et al. (1990). Eds. Academic Press, San Diego, Calif. pp 13-20; Wharam et al. (2001). *Nucleic Acids Res.* 29(11): E54-E54; Hafner et al. (2001). *Biotechniques*. 30(4): 852-6, 858, 860 passim. Further amplification methods suitable for use with the present methods include, for example, reverse transcription PCR (RT-PCR), ligase chain reaction (LCR), transcription-based amplification system (TAS), nucleic acid sequence based amplification (NASBA) reaction, self-sustained sequence replication (3SR), strand displacement amplification (SDA) reaction, boomerang DNA amplification (BDA), Q-beta replication, or isothermal nucleic acid sequence based amplification.

As used herein, the term "forward primer" refers to a primer that hybridizes to the anti-sense strand of dsDNA. A "reverse primer" hybridizes to the sense-strand of dsDNA.

As used herein, the term "genomic DNA" refers to some or all of the DNA from the nucleus of a cell. Genomic DNA may be intact or fragmented (e.g., digested with restriction endonucleases by methods known in the art). In some embodiments, genomic DNA may include sequences from all or a portion of a single gene or from multiple genes, sequences from one or more chromosomes, or sequences from all chromosomes of a cell.

As used herein, the terms "hybridize" and "hybridization" refer to a process where two complementary or partially-complementary nucleic acid strands anneal to each other as a result of Watson-Crick base pairing. Nucleic acid hybridization techniques are well known in the art. See, e.g., Sambrook, et al., 1989, *Molecular Cloning: A Laboratory Manual*, Second Edition, Cold Spring Harbor Press, Plainview, N.Y. Those skilled in the art understand how to estimate and adjust the stringency of hybridization conditions such that sequences having at least a desired level of complementarities will form stable hybrids, while those having lower complementarities will not. For examples of hybridization conditions and parameters, see, e.g., Sambrook, et al., 1989, *Molecular Cloning: A Laboratory Manual*, Second Edition, Cold Spring Harbor Press, Plainview, N.Y.; Ausubel, F. M. et al. 1994, *Current Protocols in Molecular Biology*. John Wiley & Sons, Secaucus, N.J.

As used herein, the term "nucleic acid" refers broadly to genomic DNA, segments of a chromosome, segments or portions of DNA, cDNA, and/or RNA. Nucleic acids may be derived or obtained from an originally isolated nucleic acid sample from any source (e.g., isolated from, purified from, amplified from, cloned from, reverse transcribed from sample DNA or RNA). Nucleic acids include those resident in a biological sample, preferably a cell sample or a cellular body fluid sample.

As used herein, the term "sense strand" means the strand of double-stranded DNA (dsDNA) that includes at least a portion of a coding sequence of a functional protein. "Anti-sense strand" means the strand of dsDNA that is the reverse complement of the sense strand.

As used herein, the term "swab sample" means a sample obtained with a collection tool. The collection tool may include a small piece of cotton or soft porous foam on the end of the tool, but is not required to.

Referring now to the drawing figures, wherein like reference numerals identify similar, identical, or corresponding elements, embodiments of the direct nucleic acid analysis apparatus and methods of using and producing the same are described.

In general, the methods of the present disclosure involve contacting a swab sample with nucleic acid amplification reagents without purification of nucleic acids in the swab sample and then performing a nucleic acid amplification reaction on a nucleic acid template in the swab sample. In some embodiments, the nucleic acid amplification reagents contain DNA polymerase at a concentration higher than typically used in PCR reactions (1.0 U/reaction); primer and probe concentrations higher than typically used in PCR reactions (0.1-0.2 µM); or the combination of the two conditions.

In some embodiments, the methods further comprise determining whether an amplification product was produced as a result of the nucleic acid amplification reaction.

Collection of Samples

In general, the swab sample is collected by contacting a sample source with a physical structure. Any physical structure that collects a swab sample when contacted with the sample source may be used for this purpose. In some embodiments, the physical structure may comprise an absorbent material (e.g., cotton). In some embodiments, the physical structure may be made of plastic and may collect the swab sample as a result of friction.

In some embodiments, the swab sample may be collected using a buccal swab such as the EASYSWAB (TrimGen, Cat. No. ES-100). In some embodiments, the nucleic acid amplification reaction is performed in a reaction vessel 100, which has a cap 101 (e.g., the cap of a Spartan DX-12 tube as shown in FIGS. 1-4), which cap is used to collect the swab sample. It is to be understood that any cap configuration may be used for this purpose. In some embodiments cap 101 is made of a plastic material. In some embodiments, cap 101 has a tip 106 that protrudes inside the reaction vessel 103 as shown in FIGS. 1-4. Tip 106 of cap 101 is used to collect the buccal sample. In some embodiments, cap 101 is separated from the body of the reaction vessel for this collection step, as shown in FIG. 4, while in other embodiments cap 101 remains connected to the body of reaction vessel 103 via a flexible arm or cord (not shown).

Figure 2:
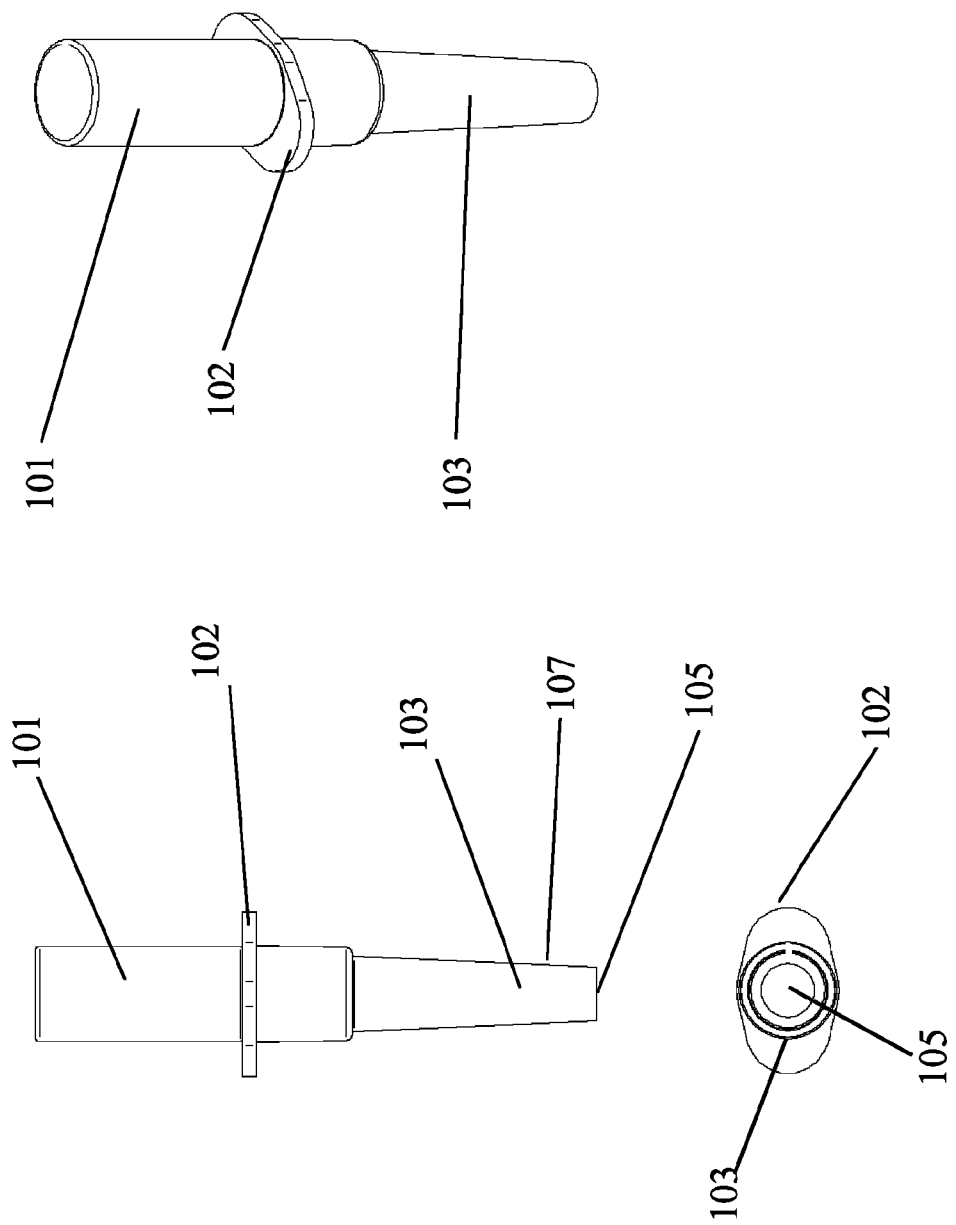
FIG. 2 shows front, bottom, and perspective views of a Spartan DX-12 tube of FIG. 1 with the cap fully inserted.
Figure 3:
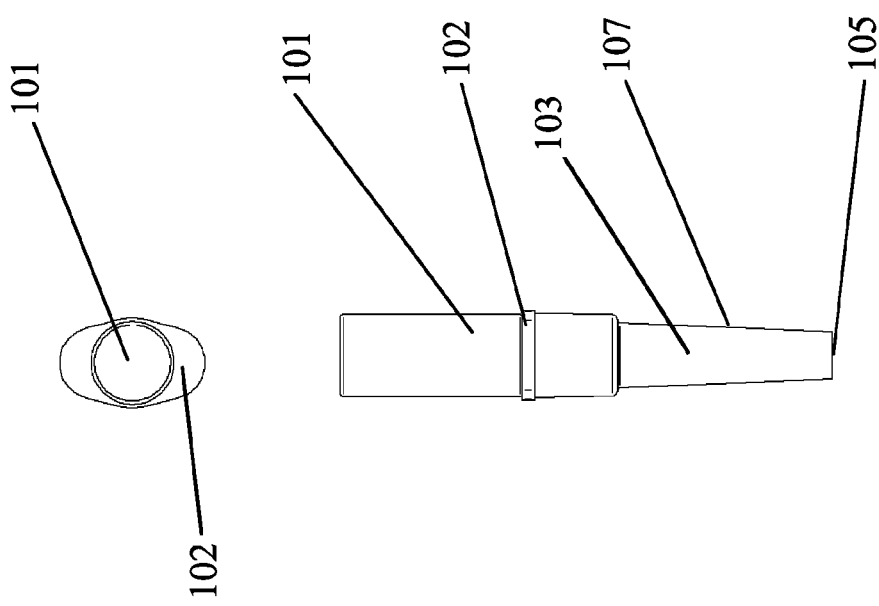
FIG. 3 shows side and top views of a Spartan DX-12 tube of FIG. 1 with the cap fully inserted.
Figure 4:
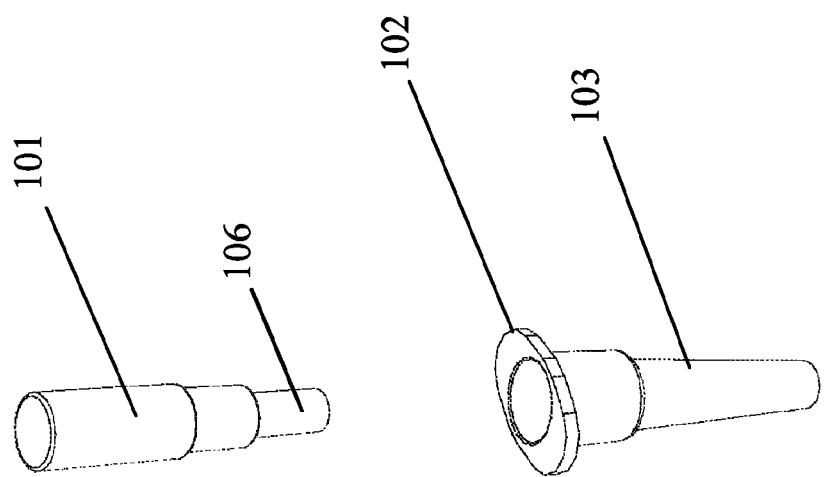
FIG. 4 shows perspective views of a Spartan DX-12 tube of FIG. 1 with the cap removed from the tube.

FIGS. 2-4 provide additional view of the cap and reaction vessel illustrated in FIG. 1. FIG. 2 shows front, bottom, and perspective views of a Spartan DX-12 tube of FIG. 1 with the cap fully inserted. As demonstrated in FIGS. 1-4 the tube body of reaction vessel 103 may have be tapered, for example at a 5° angle, in accordance with various embodiments of the present invention. FIG. 3 shows side and top views of a Spartan DX-12 tube of FIG. 1 with the cap fully inserted. The side view provided by FIG. 3 illustrates that lip 102 of tube 103 may extend on only a portion of the periphery of the tube. FIG. 4 shows perspective views of a Spartan DX-12 tube of FIG. 1 with the cap removed from the tube. As further demonstrated in FIG. 4, tip 106 of cap 101 may contain a series of graduations such that the outer diameters of the tip substantially corresponding to the various inner diameters of tube 103.

Figure 5:
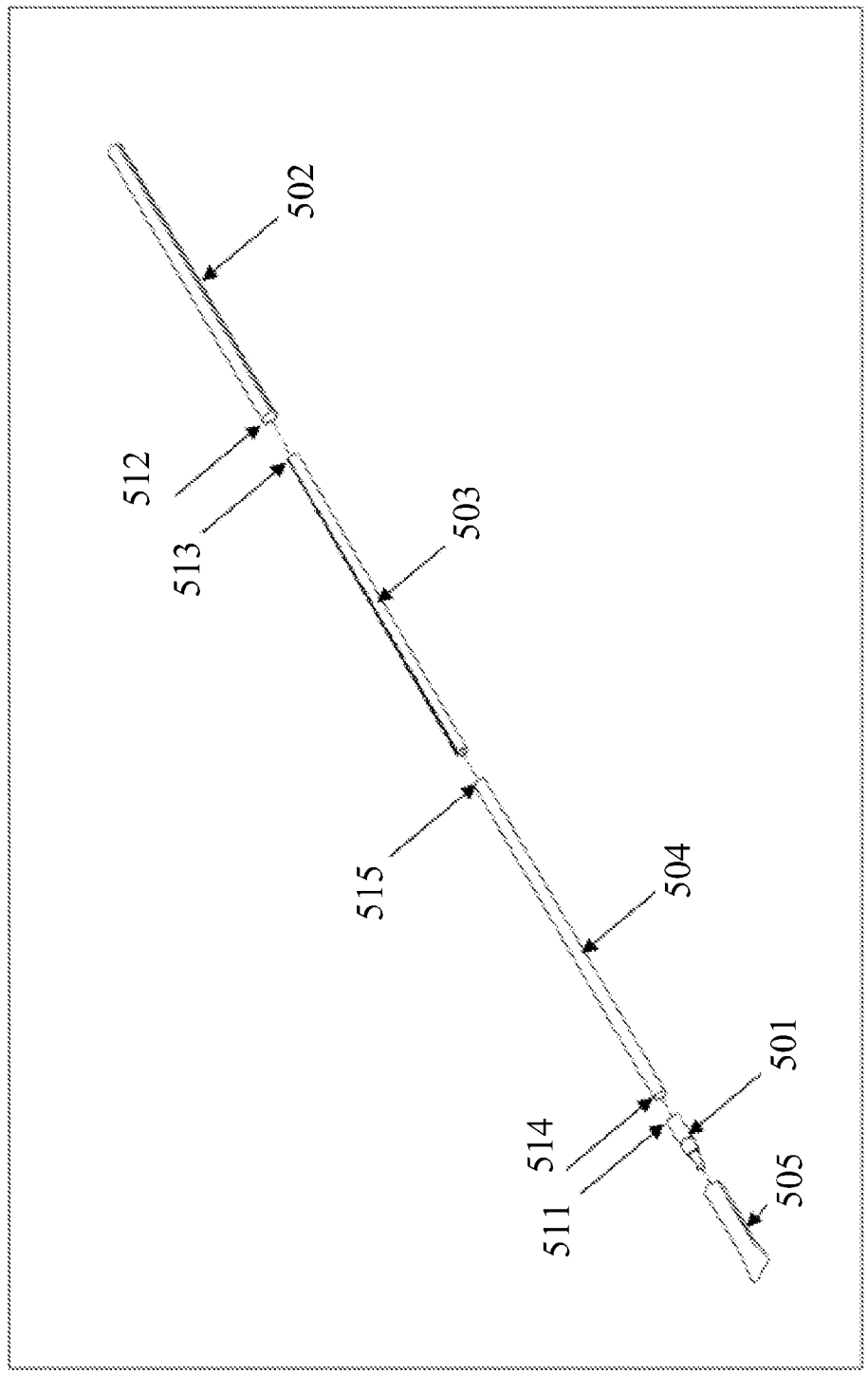
FIG. 5 shows how a cap from a Spartan DX-12 tube may be assembled with an exemplary means for holding the cap in accordance with embodiments of the present invention.
Figure 6:
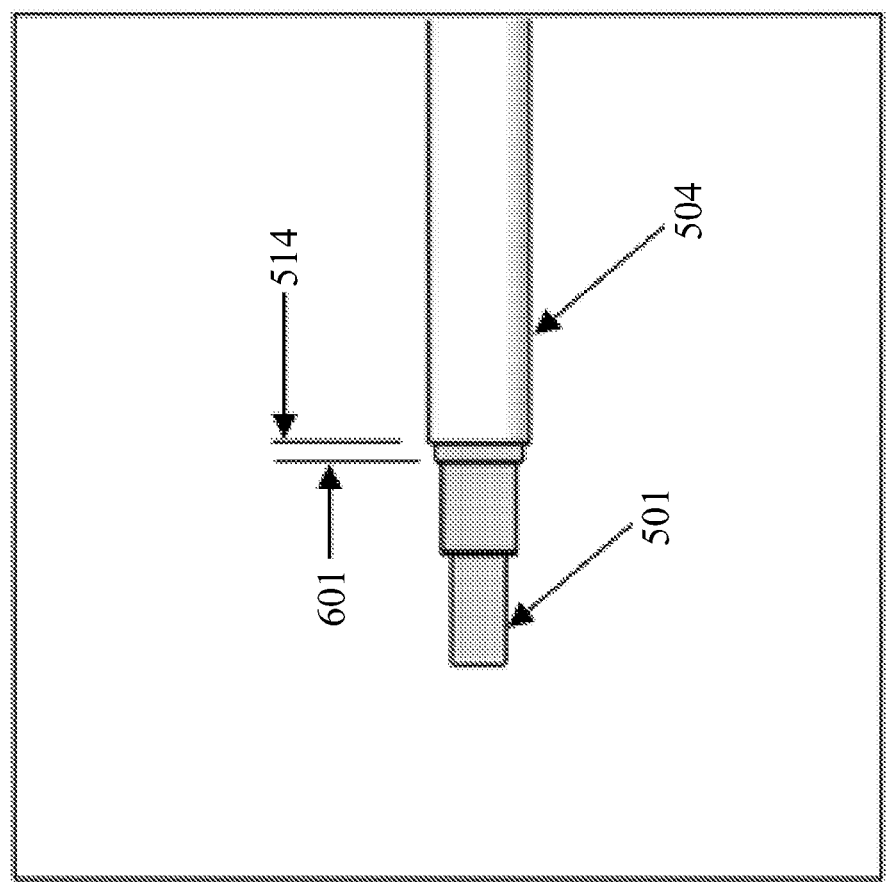
FIG. 6 shows how the cap and means for holding the cap shown in FIG. 5 are mated.

In some embodiments, a means for holding cap 101 of the reaction vessel 103 is used when collecting the swab sample. Any structure that is capable of holding cap 101 may be used for this purpose. In some embodiments, at least a portion of tip 106 of cap 101 is formed into a shape corresponding to at least a portion of the shape of the inner volume of reaction vessel 103, such that the vessel and tip engage in a mating configuration. The end of cap 101 opposing tip 106 is shaped to engage in a mating configuration with means for holding the cap in accordance with some embodiments of the present invention. Exemplary structures for holding cap 101 are shown in FIGS. 5-6, as discussed further herein.

In some embodiments, the swab sample is collected from a mammal (e.g., a human, dog, cat, cow, sheep, pig, etc.). In some embodiments, the mammal is a human. In some embodiments, the swab sample is collected from an open body cavity (e.g., mouth, nose, throat, ear, rectum, vagina, and wound). In some embodiments, the swab sample is a buccal sample. In some embodiments, the buccal sample may be collected by contacting (e.g., touching and/or swiping) cap 101 on the inside of a cheek. In some embodiments, the buccal sample may be collected by contacting cap 101 with a tongue rather than a cheek. In some embodiments, the swab sample is collected from a body surface (e.g., skin). In some embodiments, the swab sample is collected from the palm of a hand, inside the folds of the pinna of an ear, an armpit, or inside a nasal cavity. Any of the aforementioned samples may be obtained by touching and/or swiping the relevant surface with a physical structure (e.g., a buccal swab or cap 101 of reaction vessel 103).

In some embodiments, the swab sample is collected from a foodstuff. In some embodiments, the foodstuff is raw. In some embodiments, the foodstuff is a fruit, a vegetable, a meat, a fish, or a shellfish. In some embodiments, the meat is pork, beef, chicken or lamb. In some embodiments, the swab sample may be collected by touching and/or swiping the relevant foodstuff.

In general, two or more buccal samples may be collected from the same source and subsequently processed according to the methods of the present disclosure. As discussed in connection with examples provided herein, testing two or more samples from the same source may reduce and even eliminate situations where no results are obtained for a particular source. In some embodiments, the two or more samples may be collected from about the same location within the source (e.g., both from the inner cheek or both from the tongue in the case of a buccal sample). In some embodiments, the samples may be collected from different locations (e.g., one from the cheek and one from the tongue in the case of a buccal sample). In yet other embodiments, one sample may be collected and split into two aliquots that are then processed separately. In some embodiments, one sample is collected with a reaction vessel cap or buccal swab and the cap or swab is then sequentially contacted with nucleic acid amplification reagents in separate reaction vessels. In some embodiments a cap is used for this purpose and used to cap off the second reaction vessel (a fresh sterile cap being used to cap off the first reaction vessel). In general, it is to be understood that the two or more samples may be processed in sequence, in parallel or a combination thereof.

In some embodiments, the swab sample may be collected from a subject using cap 101 of reaction vessel 103, such as the Spartan DX-12 tube cap (Spartan Bioscience, Ottawa, Canada). It is to be understood that any cap configuration may be used for this purpose. In some embodiments, the cap may be held by a cap holder device such as in the Spartan swab (Spartan Bioscience, Ottawa, Canada).

Amplification of Nucleic Acids

As detailed herein, samples, which may be buccal swab samples, are collected and contacted with nucleic acid amplification reagents without purification of nucleic acids in the sample. In certain embodiments, the term "without purification" means that the nucleic acids in the sample are not subjected to a purification technique that involves physically or chemically separating nucleic acids from other components in the cells that originally contained the nucleic acids. In some embodiments, "without purification" means not performing any step or steps that remove a percentage of the non-nucleic acid components of the sample greater than or equal to 1%, 2%, 3%, 4%, 5%, 10%, 20% or more prior to contacting the sample with a nucleic acid amplification reagent.

In certain embodiments, the collected buccal samples may be directly contacted with nucleic acid amplification reagents without any intervening steps. This may be achieved by, for example, placing nucleic acid amplification reagents in a reaction vessel, using the cap of the vessel to collect a buccal sample, immediately inserting the cap into the reaction vessel, and then bringing the nucleic acid amplification reagents into contact with the buccal sample (e.g., by flicking the reaction vessel, inverting the reaction vessel, shaking the reaction vessel, vortexing the reaction vessel, etc.). Similarly, when using a swab to collect buccal samples, the swab may be dipped directly into the nucleic acid amplification reagents.

In certain embodiments, the collected swab samples may be subjected to an intervening step before being contacted with nucleic acid amplification reagents. For example, as discussed above, in certain situations it may be advantageous to divide a swab sample into aliquots so that more than one test may be performed for the same sample source. In some embodiments, a swab sample may be diluted in a vessel other than the reaction vessel (e.g., by mixing the swab sample with a buffer) and optionally aliquoted before contacting the nucleic acid amplification reagents in the reaction vessel. Those skilled in the art will recognize that other similar intervening steps could be introduced into a method of the present disclosure without deviating from the scope of various embodiments of the present invention.

In various embodiments, template nucleic acids from the buccal sample may be amplified using polymerase chain reaction (PCR) or reverse transcription PCR (RT-PCR); however, as noted previously, the skilled artisan will understand that numerous methods are known in the art for amplification of nucleic acids, and that these methods may be used either in place of, or together with, PCR or RT-PCR. For example, without limitation, other amplification methods employ ligase chain reaction (LCR), transcription-based amplification system (TAS), nucleic acid sequence based amplification (NASBA) reaction, self-sustained sequence replication (3SR), strand displacement amplification (SDA) reaction, boomerang DNA amplification (BDA), Q-beta replication, isothermal nucleic acid sequence based amplification, etc. In general, nucleic acid amplification methods, such as PCR, RT-PCR, isothermal methods, rolling circle methods, etc., are well known to the skilled artisan. See, e.g., Saiki, "Amplification of Genomic DNA" in *PCR Protocols*, Innis et al. (1990). Eds. Academic Press, San Diego, Calif. pp 13-20; Wharam et al. (2001). *Nucleic Acids Res.* 29(11): E54-E54; Hafner et al. (2001). *Biotechniques.* 30(4): 852-6, 858, 860 passim.

In certain embodiments, the nucleic acid amplification reagents that are involved in each of these amplification methods contain DNA polymerase at a concentration higher than typically used in PCR reactions (1.0 U/reaction). In various embodiments, the DNA polymerase concentration is 2.0 U/reaction. The nucleic acid amplification reagents that are involved in each of these amplification methods (e.g., enzymes, primers, probes, buffers, etc.) may vary but are also well known in the art and readily available from commercial sources (e.g., see catalogues from Invitrogen, Biotools, New England Biolabs, Bio-Rad, QIAGEN, Sigma-Aldrich, Agilent Technologies, R&D Systems, etc.). It will also be appreciated that the specific primers and/or probes that are used in any given method will depend on the template nucleic acid and the target sequence that is being amplified and that those skilled in the art may readily design and make suitable primers and/or probes for different template nucleic acids and target sequences. Primers and probes may also be prepared by commercial suppliers (e.g., Integrated DNA Technologies).

In another embodiment, the nucleic acid amplification reagents contain primer and probe concentrations higher than typically used in PCR reactions (0.1-0.2 µM). In some embodiments, the primer concentration is 0.5 µM and the probe concentration is 0.7 µM.

In another embodiment, the nucleic acid amplification reagents contain both DNA polymerase, primer, and probe concentrations higher than typically used in PCR reactions. In some embodiments, the DNA polymerase primer concentration is 2.0 U/reaction; the primer concentration is 0.5 µM; and the probe concentration is 0.7 µM.

PCR is a technique for making many copies of a specific target sequence within a template DNA. The reaction consists of multiple amplification cycles and is initiated using a pair of primer oligonucleotides that hybridize to the 5' and 3' ends of the target sequence. The amplification cycle includes an initial denaturation and typically up to 50 cycles of hybridization, strand elongation (or extension), and strand separation (denaturation). The hybridization and extension steps may be combined into a single step. In each cycle of the reaction, the target sequence between the primers is copied. Primers may hybridize to the copied DNA amplicons as well as the original template DNA, so the total number of copies increases exponentially with time/PCR cycle number. In some embodiments, PCR may be performed according to methods described in Whelan et al. (1995). *Journal of Clinical Microbiology.* 33(3):556-561. Briefly, the nucleic acid amplification reagents (PCR reaction mixture) include two specific primers per target sequence, dNTPs, a DNA polymerase (e.g., approximately 0.25 U of the enzyme Taq polymerase), and a buffer (e.g., 1×PCR Buffer. The amplification reaction itself is performed using a thermal cycler. Cycling parameters may be varied, depending on, for example, the melting temperatures of the primers or the length of the target sequence(s) to be extended. As mentioned previously, the skilled artisan is capable of designing and preparing primers that are appropriate for amplifying a target sequence. The length of the amplification primers for use in the present methods depends on several factors including the level of nucleotide sequence identity between the primers and complementary regions of the template nucleic acid and also the temperature at which the primers are hybridized to the template nucleic acid. The considerations necessary to determine a preferred length for an amplification primer of a particular sequence identity are well-known to a person of ordinary skill in the art and include considerations described herein. For example, the length and sequence of a primer may relate to its desired hybridization specificity or selectivity.

In certain embodiments, the nucleic acid amplification reaction is performed within 120 minutes of contacting the buccal sample with the nucleic acid amplification reagents. In some embodiments, the nucleic acid amplification reaction is performed even sooner, e.g., within 60, 30, 15, 10, 5 or even 1 minute(s) of contacting the swab sample with the nucleic acid amplification reagents.

In certain embodiments, the nucleic acid amplification reaction comprises an initial heat denaturation step of 15 minutes or less. In some embodiments, the initial heat denaturation step is shorter, e.g., 5 minutes or less, 3 minutes or less, or 1 minute or less. In certain embodiments, the initial heat denaturation step is performed at a temperature in the range of about 85° C. to about 99° C., e.g., about 93° C. to about 97° C., about 93° C. to about 95° C., or about 95° C. to about 97° C., etc. In some embodiments, the initial heat denaturation step is performed at about 95° C.

Detection of Nucleic Acids

The presence of amplified target sequences or amplicons may be detected by any of a variety of well-known methods. For example, in some embodiments electrophoresis may be used (e.g., gel electrophoresis or capillary electrophoresis). Amplicons may also be subjected to differential methods of detection, for example, methods that involve the selective detection of variant sequences (e.g., detection of single nucleotide polymorphisms or SNPs using sequence specific probes). In some embodiments, amplicons are detected by real-time PCR.

Real-time PCR or end-point PCR may be performed using probes in combination with a suitable amplification/analyzer such as the Spartan DX-12 desktop DNA analyzer, which is a low-throughput PCR system with fluorescent detection capabilities. Briefly, probes specific for the amplified target sequence (e.g. molecular beacons, TaqMan probes) are included in the PCR amplification reaction. For example, molecular beacons contain a loop region complementary to the target sequence of interest and two self-complementary stem sequences at the 5' and 3' end. This configuration enables molecular beacon probes to form hairpin structures in the absence of a target complementary to the loop. A reporter dye is positioned at the 5' end and a quencher dye at the 3' end. When the probes are in the hairpin configuration, the fluorophore and quencher are positioned in close proximity and contact quenching occurs. During PCR, the fluorescently labeled probes hybridize to their respective target sequences; the hairpin structure is lost, resulting in separation of the fluorophore and quencher and generation of a fluorescent signal. In another example, TaqMan probes contain a reporter dye at the 5' end and a quencher dye at the 3' end. During PCR, the fluorescent labeled TaqMan probes hybridize to their respective target sequences; the 5' nuclease activity of the DNA polymerase (e.g., Taq polymerase) cleaves the reporter dye from the probe and a fluorescent signal is generated. When probes that hybridize to different target sequences are used, these are typically conjugated with a different fluorescent reporter dye. In this way, more than one target sequence may be assayed for in the same reaction vessel. The increase in fluorescence signal is detected only if the target sequence is complementary to the probe and is amplified during PCR. A mismatch between probe and target sequences greatly reduces the efficiency of probe hybridization and cleavage.

The Spartan DX-12 has the capability to measure fluorescence at the beginning and end of the PCR thermal cycling, providing convenient "end-point" detection of amplicon accumulation.

Kits

The present disclosure also provides a kit comprising a reaction vessel, a cap for the reaction vessel, and a means for holding the cap, wherein the cap comprises a tip that is capable of protruding into and mating with the reaction vessel and an end opposing the tip that is capable of mating with the means for holding the cap.

In some embodiments, the kit further comprises nucleic acid amplification reagents. In some embodiments, the cap is mated with the reaction vessel and the nucleic acid amplification reagents are located within the reaction vessel. In some embodiments, the reaction vessel is empty and the nucleic acid amplification reagents are located within one or more containers that form part of the kit.

In some embodiments, the cap is mated with the reaction vessel. In some embodiments, the cap is mated with the means for holding the cap. In some embodiments, the reaction vessel and cap are as shown in FIGS. 1-4. In some embodiments, the means for holding the cap is as shown in FIG. 5-6.

In some embodiments, the kit further comprises a means for controlling a nucleic acid amplification reaction in the reaction vessel. In some embodiments, the means for controlling a nucleic acid amplification reaction in the reaction vessel comprises a thermal cycler with a well for receiving the reaction vessel. It will be appreciated that any thermal cycler may be used for this purpose.

In some embodiments, the kit further comprises a means for determining whether an amplification product has been produced as a result of the nucleic acid amplification reaction.

In some embodiments, the means for determining whether an amplification product has been produced as a result of the nucleic acid amplification reaction comprises a device for measuring fluorescence in the reaction vessel while the reaction vessel is located within the means for controlling a nucleic acid amplification reaction in the reaction vessel.

In some embodiments the components of the kit operate as follows. First, a swab sample is collected by contacting the cap of the reaction vessel (e.g., a Spartan DX-12 tube) with the sample source, then the cap is directly contacted with nucleic acid amplification reagents (e.g., primers, dNTPs, DNA polymerase and buffer) that have been loaded into the reaction vessel. The tube is then placed in the thermal cycler (e.g., of a Spartan DX-12 instrument) where a nucleic acid amplification reaction takes place as a result of thermal cycling. The amplification products are detected using a system that is capable of detecting fluorescence within the reaction vessels when loaded within the thermal cycler (e.g., the detection components of the Spartan DX-12 instrument). Finally, the fluorescent results are manually or automatically analyzed to determine (and optionally quantify) whether an amplification product has been produced as a result of the nucleic acid amplification reaction (e.g., with the Spartan Analyzer Software or with Microsoft™ Excel™).

EXAMPLES

The following examples serve to illustrate the present invention. These examples are in no way intended to limit the scope of the invention.

Example 1

Figure 7:
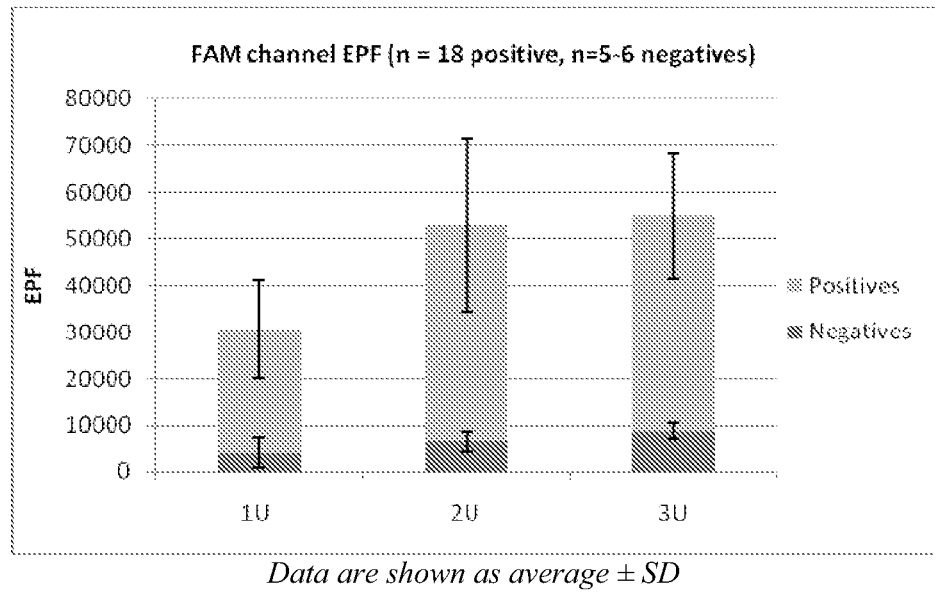
FIG. 7 shows a graph demonstrating the effect that the concentration of Taq DNA polymerase has on the Endpoint Florescence (EPF) of buccal samples amplified by a FAM probe in accordance with embodiments of the present invention.
Figure 8:
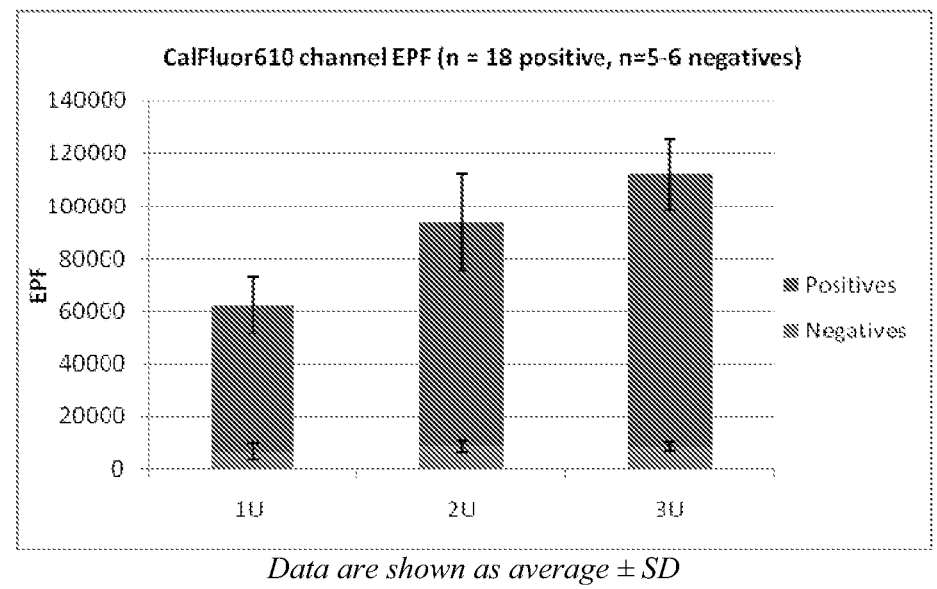
FIG. 8 shows a graph demonstrating the effect that the concentration of Taq DNA polymerase has on the Endpoint Florescence (EPF) of buccal samples amplified by a CalFluor 610 probe in accordance with embodiments of the present invention.

Effect of the Amount of Taq DNA Polymerase on PCR Performance when Amplifying from Buccal Samples FIGS. 7 and 8 show graphs demonstrating effects of concentration of Taq DNA polymerase has on the Endpoint Florescence (EPF) of buccal samples amplified by a FAM probe and a CalFluor 610 probe in accordance with embodiments of the present invention. Three buccal swabs were collected per individual by the same two technicians. Subjects were asked to rinse their mouths once with water prior to sample collection. The technicians collected buccal samples using the cap of a Spartan tube (Spartan Bioscience, Ottawa, Canada) connected to a cap holder device (Spartan swab) (Spartan Bioscience, Ottawa, Canada). The part of the cap which fits inside the Spartan tube was swiped on the inside of each subject's cheek (one swipe up, one swipe down, repeated 3 to 4 times). The cap was then inserted into a tube containing PCR master mix, and the tube was tapped gently to ensure contact between the master mix and the part of the cap containing the buccal sample. Each of the three samples collected from an individual were added to PCR master mix containing either 1 U, 2 U or 3 U GoTaq polymerase (Promega). The procedure was performed multiple times on a total of six individuals, such that 18 reactions were performed at each amount of GoTaq.

PCR primers were designed to amplify a 91 base pair amplicon from the human CYP 2C19 gene. The forward primer sequence was 5'-TgC AAT AAT TTT CCC ACT ATC ATT g-3' (SEQ ID NO:1) and the reverse primer sequence was 5'-CCA AAA TAT CAC TTT CCA TAA AAg CA-3' (SEQ ID NO:2). Primers were manufactured by Integrated DNA Technologies. The molecular beacon probe sequence for the wild-type gene was 5'-cgcagATTTCCC[G]GGAAC- CCctgcg-3' (SEQ ID NO:3). The probe was labeled at the 5' end with FAM and at the 3' end with Black Hole Quencher-1 (BHQ1). The square brackets indicate the location of the wild-type single nucleotide polymorphism (SNP). The stem portion of the molecular beacon is shown in lower case and the loop portion is shown in upper case. The molecular beacon probe sequence for the mutant gene was 5'-cgcagT-TATTTCCC[A]GGAACCCctgcg-3' (SEQ ID NO:4). The probe was labeled at the 5' end with CalFluor 610 (CF610) and at the 3' end with Black Hole Quencher-2 (BHQ2). The brackets indicate the location of the mutant SNP. The stem portion of the molecular beacon is shown in lower case and the loop portion is shown in upper case. Probes were manufactured by Biosearch Technologies. All individuals included in the study were known to carry both a wild-type and a mutant allele and are therefore expected to be successful for PCR and generate a fluorescent signal for both probes.

The PCR master mix contained final concentrations of the following components:
Colorless PCR buffer (containing final 1.5 mM magnesium chloride) (Promega, Cat. No. M792A): 1×
Additional magnesium chloride (Biotools): 2.5 mM
dNTPs (Invitrogen, Cat. No. 55082, 55083, 55084, 55085): 0.2 mM
Forward primer: 0.5 μM
Reverse primer: 0.5 μM
FAM probe: 0.7 μM
CalFluor 610 probe: 0.7 μM
GoTaq DNA polymerase (Promega, Cat. No. M400): 1 Unit/2 Units/3 Units The PCR reaction volume was 20 μl. Positive reactions contained buccal samples from individuals as detailed above. Negative control samples contained no buccal material. A total of 18 positive reactions and 5-6 negative control reactions were performed at each condition (1 U, 2 U, 3 U Taq) were performed. PCR was performed using the Spartan DX-12 instrument (Spartan Bioscience) in Spartan DX-12 tubes (Spartan Bioscience).

The PCR program had the following steps:
1) Initial denaturation: 95° C. for 5 min for 1 cycle
2) Cycling denaturation: 95° C. for 1 sec for 50 cycles
3) Cycling hybridization/extension: 45° C. for 20 sec for 50 cycles Results were analyzed using Microsoft™ Excel™. Endpoint fluorescence (EPF) was calculated for the FAM and CalFluor610 channels as the difference between fluorescence levels at the first and last cycles of the PCR.

As shown in FIGS. 7 and 8, the final EPF was higher for samples containing 2 U or 3 U of Taq DNA polymerase than for samples containing 1 U of Taq DNA polymerase for both the FAM channel and the CalFluor 610 channel. Specifically, the average and standard deviation (SD) EPF values were as follows:

|  | FAM channel EPF | | CalFluor 610 channel EPF | |
| --- | --- | --- | --- | --- |
|  | Average | SD | Average | SD |
| Negative control-1 U | 4267.2 | 3324.6 | 6769.2 | 3028.4 |
| Positive-1 U | 26364.4 | 10567.3 | 55509.9 | 18569.8 |
| Negative control-2 U | 6608.5 | 2167.5 | 8844.7 | 2383.6 |
| Positive-2 U | 46167.5 | 18522.6 | 84967.5 | 23500.3 |
| Negative control-3 U | 8862.5 | 1780.8 | 8741.2 | 2151.3 |
| Positive-3 U | 45972.8 | 13475.2 | 103321.2 | 25401.1 |

The results demonstrate that the use of Taq DNA polymerase at amounts greater than that typically employed in PCR reactions (1 U/reaction) allows for superior discrimination between positive and negative samples when amplifying directly from buccal samples without purification. This is especially important considering the wide range of human DNA in buccal and saliva samples.

Example 2

Figure 9:
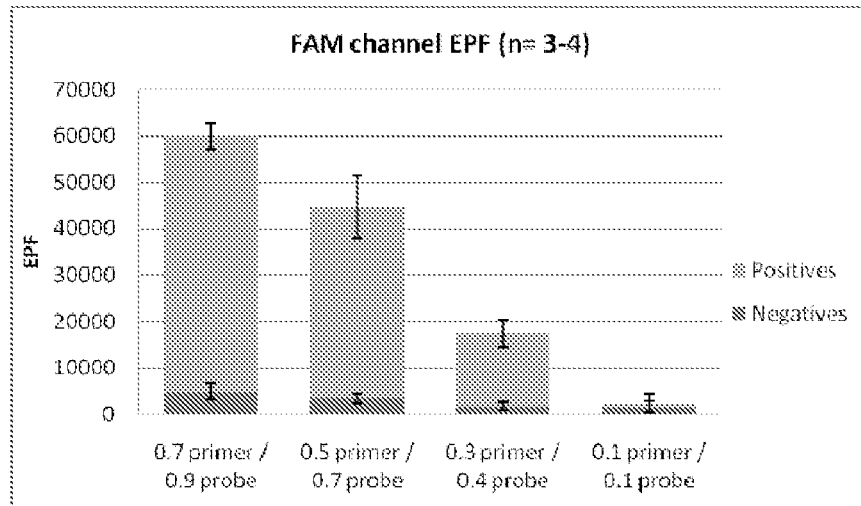
FIG. 9 shows a graph demonstrating the effect that the concentrations of primer and probe have on the Endpoint Florescence (EPF) of buccal samples amplified by a FAM probe in accordance with embodiments of the present invention.
Figure 10:
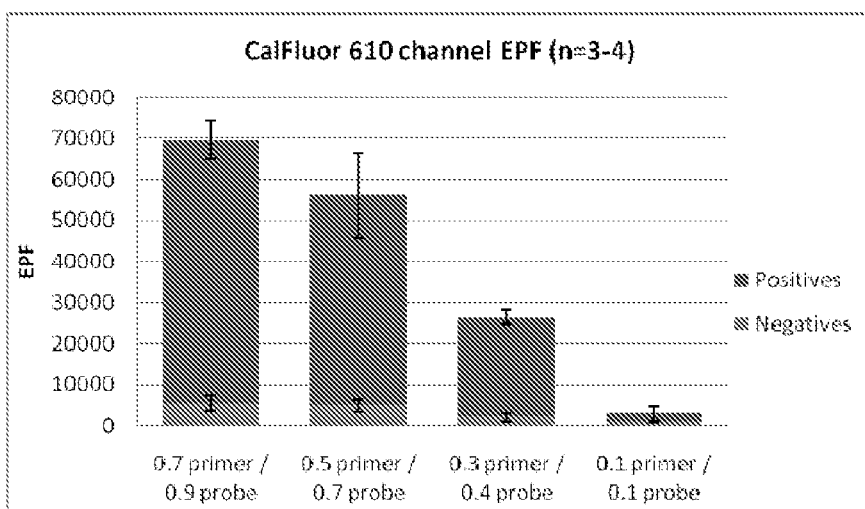
FIG. 10 shows a graph demonstrating the effect that the concentrations of primer and probe have on the Endpoint Florescence (EPF) of buccal samples amplified by a CalFluor 610 probe in accordance with embodiments of the present invention.

Effect of Primer and Probe Concentrations on PCR Performance when Amplifying from Buccal Samples FIGS. 9 and 10 show graphs demonstrating effects of concentration of primer and probe on Endpoint Florescence (EPF) of buccal samples amplified by a FAM probe and by a CalFluor 610 probe in accordance with embodiments of the present invention. Four buccal swabs per individual were collected from four individuals by the same two technicians in a single session. Subjects were asked to rinse their mouths once with water prior to sample collection. The technicians collected buccal samples as described in Example 1. The cap was then inserted into a tube containing PCR master mix, and the tube was tapped gently to ensure contact of the liquid with the part of the cap containing the buccal sample. One of each of the four samples collected from an individual was added to PCR master mix containing the following final concentrations of primers and probes:

| [Primer] (μM) | [Probe] (μM) |
| --- | --- |
| 0.7 | 0.9 |
| 0.5 | 0.7 |
| 0.3 | 0.4 |
| 0.1 | 0.1 |

PCR primers and probes were designed to amplify a 91 base pair amplicon from the human CYP 2C19 gene. The primers and probes used were as described in Example 1. All individuals included in the study were known to carry both a wild-type and a mutant allele and are therefore expected to be successful for PCR and generate a fluorescent signal for both probes.

The PCR master mix contained final concentrations of the following components:
Colorless PCR buffer (containing final 1.5 mM magnesium chloride) (Promega, Cat. No. M792A): 1×
Additional magnesium chloride (Biotools): 2.5 mM
dNTPs (Invitrogen, Cat. No. 55082, 55083, 55084, 55085): 0.125 mM
Forward primer: 0.1-0.7 μM (see table above)
Reverse primer: 0.1-0.7 μM (see table above)
FAM probe: 0.1-0.9 μM (see table above)
CalFluor 610 probe: 0.1-0.9 μM (see table above)
GoTaq DNA polymerase (Promega, Cat. No. M400): 2 Units The PCR reaction volume was 20 μl. Positive reactions contained buccal samples from individuals as detailed above. Negative control samples contained no buccal material. A total of 3-4 negative control reactions and 4 positive reactions were performed for each primer/probe concentration. PCR was performed using the Spartan DX-12 instrument (Spartan Bioscience, Ottawa, Canada) in Spartan DX-12 tubes (Spartan Bioscience, Ottawa, Canada).

The PCR program had the following steps:
1) Initial denaturation: 95° C. for 5 min for 1 cycle
2) Cycling denaturation: 95° C. for 5 sec for 50 cycles
3) Cycling hybridization/extension: 55° C. for 20 sec for 50 cycles Results were analyzed using Microsoft™ Excel™. Endpoint fluorescence (EPF) was calculated for the FAM and CalFluor610 channels as the difference between fluorescence levels at the first and last cycles of the PCR.

As demonstrated in FIGS. 9 and 10, increasing concentration of primers and probes to levels greater than those typically employed in standard PCR reactions (~0.1-0.2 µM) resulted in higher final EPF values and generally lower relative standard deviations for both the FAM channel and the CalFluor 610 channel. Specifically, average and standard deviation (SD) EPF values were as follows:

|  | FAM channel EPF | | CalFluor 610 channel EPF | |
| --- | --- | --- | --- | --- |
|  | Average | SD | Average | SD |
| Negative control 0.1 µM primer/0.1 µM probe | 1476.1 | 1341.2 | 1222.9 | 294.1 |
| Positive 0.1 µM primer/0.1 µM probe | 1070.0 | 1981.6 | 1859.8 | 1595.2 |
| Negative control 0.3 µM primer/0.4 µM probe | 1769.2 | 878.1 | 2142.4 | 950.8 |
| Positive 0.3 µM primer/0.4 µM probe | 15743.0 | 2900.6 | 24386.2 | 1737.6 |
| Negative control 0.5 µM primer/0.7 µM probe | 3425.9 | 907.5 | 4971.2 | 1526.1 |
| Positive 0.5 µM primer/0.7 µM probe | 41231.7 | 6753.8 | 51208.9 | 10244.6 |
| Negative control 0.7 µM primer/0.9 µM probe | 4940.4 | 1878.5 | 5534.5 | 1850.1 |
| Positive 0.7 µM primer/0.9 µM probe | 54958.5 | 2841.7 | 63985.8 | 4657.9 |

The results demonstrate that the use of primers and probes at concentrations higher than those typically employed in PCR reactions (0.1-0.2 µM) allows for superior discrimination between positive and negative samples when amplifying directly from buccal samples without purification. This is especially important considering the wide range of human DNA in buccal and saliva samples.

Example 3

Figure 11:
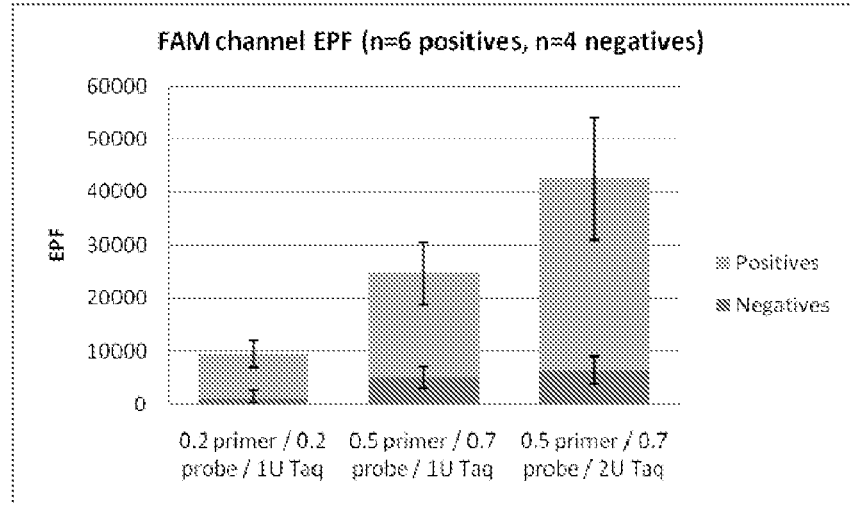
FIG. 11 shows a graph demonstrating the combined effect that the concentrations of Taq DNA polymerase, primer, and probe have on the Endpoint Florescence (EPF) of buccal samples amplified by a FAM probe in accordance with embodiments of the present invention.
Figure 12:
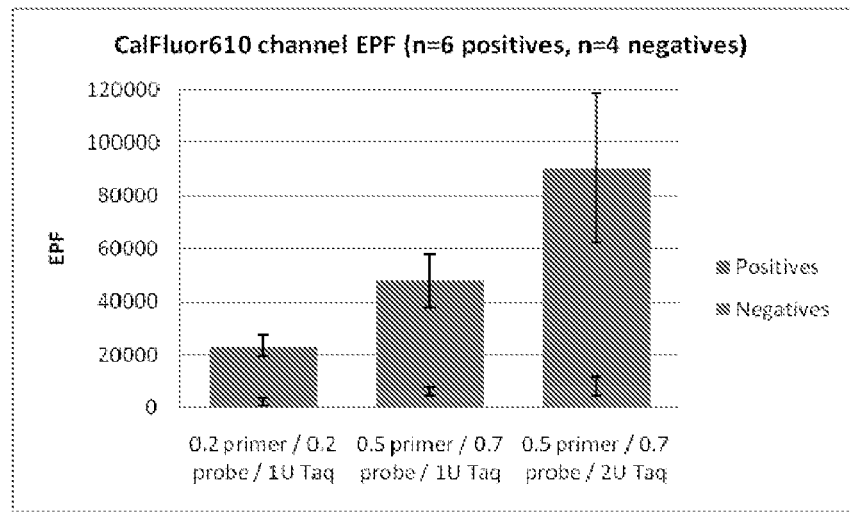
FIG. 12 shows a graph demonstrating the combined effect that the concentrations of Taq DNA polymerase, primer, and probe have on the Endpoint Florescence (EPF) of buccal samples amplified by a CalFluor 610 probe in accordance with embodiments of the present invention.

Combined Effect of Primer Concentration, Probe Concentration, and the Amount of Taq DNA Polymerase on PCR Performance when Amplifying from Buccal Samples FIGS. 11 and 12 show graphs demonstrating combined effects of concentration of Taq DNA polymerase, primer, and probe on Endpoint Florescence (EPF) of buccal samples amplified by a FAM probe and a CalFluor 610 probe, respectively, in accordance with embodiments of the present invention. Six buccal swabs per individual were collected from three individuals by the same two technicians in a single session. Subjects were asked to rinse their mouths once with water prior to sample collection. The technicians collected buccal samples as described in Example 1. The cap was then inserted into a tube containing PCR master mix, and the tube was tapped gently to ensure contact of the liquid with the part of the cap containing the buccal sample. The buccal samples collected from an individual were added to one of three PCR master mixes, containing the following final amount of Taq DNA polymerase and concentrations of primers and probes:

| [Primer] (µM) | [Probe] (µM) | Taq DNA polymerase (Units) |
| --- | --- | --- |
| 0.2 | 0.2 | 1.0 |
| 0.5 | 0.7 | 1.0 |
| 0.5 | 0.7 | 2.0 |

PCR primers and probes were designed to amplify a 91 base pair amplicon from the human CYP 2C19 gene. The primers and probes used were as described in Example 1. All individuals included in the study were known to carry both a wild-type and a mutant allele and are therefore expected to be successful for PCR and generate a fluorescent signal for both probes.

The PCR master mix contained final concentrations of the following components:
  Colorless PCR buffer (containing final 1.5 mM magnesium chloride) (Promega, Cat. No. M792A): 1×
  Additional magnesium chloride (Biotools): 2.5 mM
  dNTPs (Invitrogen, Cat. No. 55082, 55083, 55084, 55085): 0.2 mM
  Forward primer: 0.2-0.5 µM (see table above)
  Reverse primer: 0.2-0.5 µM (see table above)
  FAM probe: 0.2-0.7 µM (see table above)
  CalFluor 610 probe: 0.2-0.7 µM (see table above)
  GoTaq DNA polymerase (Promega, Cat. No. M400): 1 or 2 Units (see table above)

The PCR reaction volume was 20 µl. Positive reactions contained buccal samples from individuals as detailed above. Negative control samples contained no buccal material. A total of 4 negative controls and 6 positive reactions were performed for each PCR master mix (see table above). PCR was performed using the Spartan DX-12 instrument (Spartan Bioscience) in Spartan DX-12 tubes (Spartan Bioscience).

The PCR program had the following steps:
1) Initial denaturation: 95° C. for 5 min for 1 cycle
2) Cycling denaturation: 95° C. for 1 sec for 50 cycles
3) Cycling hybridization/extension: 45° C. for 20 sec for 50 cycles Results were analyzed using Microsoft™ Excel™. Endpoint fluorescence (EPF) was calculated for the FAM and CalFluor610 channels as the difference between fluorescence levels at the first and last cycles of the PCR.

As illustrated in FIGS. 11 and 12, in comparison to samples containing 1 U of polymerase, 0.2 µM primers and 0.2 µM probes, the final EPF was higher for samples containing 1 U of polymerase, 0.5 µM primers and 0.7 µM probes and the EPF for samples containing 2 U of polymerase, 0.5 µM primers and 0.7 µM probes was increased further for both the FAM channel and the CalFluor 610 channel. These findings demonstrate, for example, there is an additive effect of increased primer/probe concentration and increased amount of Taq. Specifically, the average and standard deviation (SD) EPF values were as follows:

|  | FAM channel EPF | | CalFluor 610 channel EPF | |
| --- | --- | --- | --- | --- |
|  | Average | SD | Average | SD |
| Negative control 0.2 µM primer/0.2 µM probe/ 1 U Taq | 1341.9 | 1101.9 | 2268.9 | 1535.5 |

-continued

|  | FAM channel EPF | | CalFluor 610 channel EPF | |
| --- | --- | --- | --- | --- |
|  | Average | SD | Average | SD |
| Positive 0.2 µM primer/0.2 µM probe/ 1 U Taq | 8052.9 | 2536.6 | 21061.7 | 4119.4 |
| Negative control 0.5 µM primer/0.7 µM probe/ 1 U Taq | 5040.8 | 2040.6 | 6402.5 | 1726.1 |
| Positive 0.5 µM primer/0.7 µM probe/ 1 U Taq | 19645.5 | 5919.6 | 41561.7 | 9964.2 |
| Negative control 0.5 µM primer/0.7 µM probe/ 2 U Taq | 6411.6 | 2709.3 | 8194.5 | 3572.5 |
| Positive 0.5 µM primer/0.7 µM probe/ 2 U Taq | 6088.5 | 11486.1 | 82200.1 | 27939.4 |

The results demonstrate that the combination of Taq DNA polymerase and primer/probe concentrations higher than those typically employed in PCR reactions produce a synergistic effect that is superior to either condition alone. This allows for superior discrimination between positive and negative samples when amplifying directly from buccal samples without purification. This is especially important considering the wide range in the amounts of human DNA found in buccal and saliva samples.

Example 4

PCR Success Rate for Buccal Samples

Buccal samples were collected using three different methods of swabbing. Subjects were asked not to eat or drink anything but water for 5 min prior to sample collection. Subjects were asked to rinse their mouths once with water prior to sample collection First, 31 individuals swiped the inside of their cheek a single time using the EASYSWAB (TrimGen, Cat. No. ES-100). The individuals then dipped and removed the end of the foam tip swab into a 75 µl solution of 1.33× PCR buffer (Biotools), 3.33 mM Magnesium Chloride (Biotools), and 0.167 mM dNTPs (Invitrogen). After the swab was removed, 15 µl was aliquoted into a Spartan DX-12 tube and mixed with 5 µl of the following solution: 0.4 µM FAM-BHQ1plus probe (sequence described below), 2.4 µM CF10-BHQ2probe (sequence described below), 2 µM PCR primers (sequences described below), and 1 unit of Taq polymerase (Biotools). The final concentrations are described below. The EASYSWAB was not simply dipped into a Spartan DX-12 tube containing PCR master mix because the EASYSWAB is too large to easily fit inside the tube.

Second, 33 individuals swiped the inside of their cheek a total of six times (one swipe up, one swipe down, repeated three times) using a cap from the Spartan DX-12 tube (Spartan Bioscience, see FIG. 1). The cap was then inserted into a tube containing PCR master mix, and the tube was tapped gently to ensure contact of the liquid with the part of the cap containing the sample.

Third, 19 individuals collected a sample by touching the cap of a Spartan DX-12 tube to their tongue once. The cap was then inserted into a tube containing PCR master mix, and the tube was tapped gently to ensure contact of the liquid with the part of the cap containing the sample.

PCR primers were designed to amplify a 91 base pair amplicon from the human CYP 2C19 gene. The forward primer sequence was 5'-TgC AAT AAT TTT CCC ACT ATC ATT g-3' (SEQ ID NO:1) and the reverse primer sequence was 5'-CCA AAA TAT CAC TTT CCA TAA AAg CA-3' (SEQ ID NO:2). Primers were manufactured by Integrated DNA Technologies. The TaqMan probe sequence for the wild-type gene was ttatttccc[g]ggaacc (SEQ ID NO:3). The probe was labeled at the 5' end with FAM and at the 3' end with Black Hole Quencher-1 plus (BHQ1plus). The brackets indicate the location of the wild-type single nucleotide polymorphism (SNP). The TaqMan probe sequence for the mutant gene was ttatttccc[a]ggaacc (SEQ ID NO:4). The probe was labeled at the 5' end with CalFluor 610 (CF610) and at the 3' end with Black Hole Quencher-2 (BHQ2). The brackets indicate the location of the mutant SNP. Probes were manufactured by Biosearch Technologies. All individuals are expected to be successful for PCR and generate a fluorescent signal for the FAM probe because all individuals tested were known to carry at least one copy of the wild-type the target allele and thus the reaction contains an internal positive control.

The PCR master mix contained final concentrations of the following components:
PCR buffer (Biotools): 1×
Magnesium chloride (Biotools): 2.5 mM
dNTPs (Invitrogen, Cat. No. 10297-018): 0.125 mM
Forward primer: 0.5 µM
Reverse primer: 0.5 µM
FAM probe: 0.1 µM
CalFluor 610 probe: 0.6 µM (included in some but not all reactions—fluorescent data for the CalFluor 610 channel was not used in the analysis)
DNA polymerase (Biotools): 1 Unit The PCR reaction volume was 20 µl. PCR was performed using the Spartan DX-12 instrument (Spartan Bioscience) in Spartan DX-12 tubes (Spartan Bioscience).

The PCR program had the following steps:
Initial denaturation: 95° C. for 15 min for 1 cycle
Cycling denaturation: 95° C. for 5 sec for 50 cycles
Cycling hybridization/extension: 50° C. for 10 sec for 50 cycles.

Results were analyzed using Microsoft™ Excel™. End-point fluorescence (EPF) was calculated for the FAM channel as the difference between fluorescence levels at the first and last cycles of the PCR. For each swabbing method tested, a reaction was deemed to have failed if the EPF value in the FAM channel was smaller than or equal to the average EPF of multiple negative control reactions containing no nucleic acid template.

For the TrimGen swab, 28 out of 31 buccal samples generated a positive PCR result, with 3 failures (90.3% reliability rate). For the Spartan cap swiped on the cheek, 30 out of 33 buccal samples generated a positive PCR result, with 3 failures (90.9% reliability rate). For the Spartan cap touched on the tongue, 17 out of 19 samples generated a positive PCR result, with 2 failures (89.5% reliability rate).

Methods that collect both more and less buccal material were also evaluated. To collect a large amount of buccal material, large-bore pipette tips were used to perform scrapes on the inside of the cheek. The large-pore pipette tips were constructed by cutting off the bottom 1 cm of a standard P1000 pipette tip. Material collected from multiple cheek scrapes was pooled and 3 µl of this material was added to a Spartan tube containing 20 µl of 1×PCR master mix. To gather a small amount of buccal material, a fine pipette tip (10 µl) was touched to the side of the mouth once (contacting the buccal epithelium) and then touched to 20 μl of 1×PCR master mix inside a Spartan tube. For both methods, the final concentrations of components of the PCR master mix were as listed above. For both methods, 12 replicate Spartan tubes were tested. Results were analyzed as described above. For the large amount of material, 12 of 12 samples generated a positive PCR result (100% reliability rate). For the small amount of material, 7 of 12 samples generated a positive PCR result (58.3% reliability rate).

Based on these results, it appears that buccal swabs enable significantly higher PCR reliability rates compared with direct amplification from whole saliva samples (Ochert A S et al. (1994). Inhibitory effect of salivary fluids on PCR: potency and removal. *Genome Research*. 3: 365-368.). Another unexpected result was that the reliability rates were high across four of the five sample collection methods (TrimGen swab, Spartan cap swiped on cheek, Spartan cap touched on tongue, Large bore pipette tip), despite the fact that these methods collect significantly different amounts of buccal material. The fact that the reliability rate decreased for samples with a low amount of material (fine pipette tip touched to the corner of the mouth) demonstrates that there is a lower limit of buccal material required for optimal reaction performance.

The range of buccal material collected by the Spartan cap methods were determined by spectrophotometric analysis of samples collected by the "Spartan DX-12 cap on cheek" and "Spartan DX-12 cap on tongue" methods. Specifically, a single individual self-collected 24 buccal samples using the "cap on cheek" technique and 12 buccal samples using the "cap on tongue" technique, as previously described. Absorbance of the samples at 230 nm, 260 nm, and 280 nm was measured by loading a 1.5 μl aliquot onto the pedestal of the NANODROP spectrophotometer (Thermo Scientific). A 1.5 μl aliquot of sterile water was used as the control sample. Each buccal sample was measured in duplicate.

Average absorbance readings for the two collection techniques were as follows:

|  | A230 | A260 | A280 | Sum (A230, A260, A280) |
|---|---|---|---|---|
| Cap on cheek (n = 24) | 0.127 | 0.123 | 0.447 | 0.697 |
| Cap on tongue (n = 12) | 0.067 | 0.049 | 0.188 | 0.304 |

Since DNA concentration is correlated with the absorbance at 260 nm, it appears that the "cap on cheek" technique collects more than twice the amount of DNA as the "cap on tongue" technique. Nevertheless, the PCR success rate of both methods was almost equivalent. This unexpected finding indicates the cap is capable of collecting a broad range of acceptable amounts of material.

Example 5

Timing for Testing of Buccal Samples

Five individuals self-collected buccal samples by swiping the inside of their cheek a single time using the EASYSWAB (TrimGen, Cat. No. ES-100). The individuals then dipped the end of the foam tip swab into a solution of PCR buffer, Magnesium chloride, and dNTPs, as described in Example 4. The resulting solution was aliquoted equally into five Spartan DX-12 tubes (15 μl per tube), and mixed with 5 μl of the following solution: 0.4 μM FAM-BHQ 1plus probe, 2.4 μM CF10-BHQ2 probe, 2 μM PCR primers, 1 unit of Taq polymerase (Biotools). This ensured that each tube had the same amount of buccal material. As a control, duplicate reactions were run using 10 ng of purified genomic DNA. The PCR primers and probes, master mix concentrations, reaction volumes, PCR cycling program, and method of analysis were the same as described in Example 4.

The tubes containing PCR master mix and buccal sample or purified DNA were incubated at room temperature for different times before performing PCR:
  Four tubes were incubated at room temperature for 0 min
  Four tubes were incubated at room temperature for 15 min
  Four tubes were incubated at room temperature for 30 min
  Four tubes were incubated at room temperature for 60 min
  Four tubes were incubated at room temperature for 90 min Results showed that the final end-point fluorescence (fluorescence at the last cycle minus fluorescence at the first cycle) was lower when the buccal sample and PCR master mix were incubated for longer times at room temperature before performing PCR. Specifically, the average ratios of final normalized end-point fluorescence achieved by reactions with buccal sample versus purified DNA were as follows:

|  | 0 min | 15 min | 30 min | 60 min | 90 min |
|---|---|---|---|---|---|
| Green probe: (FAM) ttatttccc[g]ggaacc (BHQ 1plus) (SEQ ID NO: 3) | | | | | |
| Swabs (n = 5) | 1.00 | 0.92 | 0.70 | 0.63 | 0.19 |
| Purified DNA (n = 2) | 1.00 | 0.86 | 0.80 | 0.97 | 0.55 |
| Ratio | 1.00 | 1.07 | 0.88 | 0.65 | 0.35 |
| Red probe: (CF610) ttatttccc[a]ggaacc (BHQ2) (SEQ ID NO: 4) | | | | | |
| Swabs (n = 4) | 1.00 | 0.89 | 0.67 | 0.46 | 0.20 |
| Purified DNA (n = 2) | 1.00 | 0.99 | 0.77 | 0.95 | 0.55 |
| Ratio | 1.00 | 0.90 | 0.87 | 0.48 | 0.36 |

The end-point fluorescence values declined over time the longer the buccal sample and PCR mixture was incubated at room temperature before performing the reaction. The values also decline over time for the purified DNA, but not nearly as much as for the buccal samples. Overall, the results indicate that the mixture of buccal sample and PCR master mix should ideally be tested within 15-30 minutes of contacting the sample with the PCR master mix. The practical implications of these results are significant. By minimizing the time the PCR reaction is in contact with raw sample it is possible to mitigate the effects of inhibitory substances in the sample and achieve enhanced reaction performance.

Example 6

PCR Success Rate for Buccal Samples with Different Initial Heating Times

Six individuals were instructed to swab the inside of their cheek using a buccal swab EASYSWAB, TrimGen Corp., Cat. No. ES-100). Subjects were asked not to eat or drink for 5 min prior to sample collection. Subjects were asked to rinse their mouths once with water prior to sample collection. For each subject, the buccal swab was dipped into a PCR master mix, as described in Examples 4 and 5. This master mix was then mixed and aliquoted equally into five Spartan DX-12 tubes. This ensured that each tube had the same amount of buccal material.

The PCR primers and probes, master mix concentrations and reaction volumes were the same as described in Example 4.

Results were analyzed using MICROSOFT EXCEL. Endpoint fluorescence (EPF) was calculated as the difference between fluorescence levels at the first and last cycles of the PCR. For each PCR program tested, a reaction was deemed to have failed if the EPF value was smaller than or equal to the EPF of a negative control within the same run (containing no nucleic acid template) plus 2.5 times the standard deviation of negative control reactions from all runs.

The following five PCR programs were performed (one tube for each program).

PCR Program #1:
 1) Initial denaturation: 95° C. for 15 min for 1 cycle
 2) Cycling denaturation: 95° C. for 5 sec for 50 cycles
 3) Cycling hybridization/extension: 50° C. for 10 sec for 50 cycles PCR Program #2:
 1) Initial denaturation: 95° C. for 7 min for 1 cycle
 2) Cycling denaturation: 95° C. for 5 sec for 50 cycles
 3) Cycling hybridization/extension: 50° C. for 10 sec for 50 cycles PCR Program #3:
 1) Initial denaturation: 95° C. for 5 min for 1 cycle
 2) Cycling denaturation: 95° C. for 5 sec for 50 cycles
 3) Cycling hybridization/extension: 50° C. for 10 sec for 50 cycles PCR Program #4:
 1) Initial denaturation: 95° C. for 3 min for 1 cycle
 2) Cycling denaturation: 95° C. for 5 sec for 50 cycles
 3) Cycling hybridization/extension: 50° C. for 10 sec for 50 cycles PCR Program #5:
 1) Initial denaturation: 95° C. for 1 min for 1 cycle
 2) Cycling denaturation: 95° C. for 5 sec for 50 cycles
 3) Cycling hybridization/extension: 50° C. for 10 sec for 50 cycles Results showed that an initial denaturation time of 1 min was sufficient for successful amplification of 5 out of 6 buccal samples. In contrast, an initial denaturation time of 3, 5, 7, or minutes was sufficient for successful amplification of 6 out of 6 buccal samples.

Results showed that an initial denaturation time of 1 min was sufficient for successful amplification of 5 out of 6 buccal samples. In contrast, an initial denaturation time of 3, 5, 7, or minutes was sufficient for successful amplification of 6 out of 6 buccal samples.

This result was unexpected given that the PCR success rate with whole saliva samples was reported as 7 out of 10 samples after 5 minutes of boiling followed by 1 min of cycling denaturation at 94° C. (Ochert A S et al. (1994). Inhibitory effect of salivary fluids on PCR: potency and removal. Genome Research. 3: 365-368.)

Example 7

Higher Diagnostic Success Rate by Testing Two Swabs at the Same Time from the Same Individual Buccal samples were collected from 25 individuals by the same technician. Subjects were asked not to eat or drink for 5 min prior to sample collection. The technician collected samples by taking the cap from a Spartan DX-12 tube (Spartan Bioscience) and swiping the part of the cap containing the sample inside of the cheek (one swipe up, one swipe down, repeated three times). The cap was then inserted into the tube, and the tube was tapped gently to ensure contact of the liquid with the part of the cap containing the sample of the cap. Tubes were briefly centrifuged to pull down the liquid into the bottom of the tube. Two samples were collected consecutively from each subject from roughly the same area of the cheek using a separate cap for each sample.

The PCR primers and probes, master mix concentrations, reaction volumes, PCR cycling conditions, and method of analysis were the same as described in Example 4.

For the first set of samples, the PCR success rate was 24 out of 25 samples. For the second set of samples, the PCR success rate was 23 out of 25 samples.

The unexpected result was that failed samples were from different individuals for the first and second set of samples. For example, the sample that failed PCR in the first set of samples came from an individual whose second sample resulted in a successful PCR. Similarly, the two individuals whose second samples failed PCR had first samples which resulted in successful PCR. In other words, the diagnostic success rate from collecting and testing a single sample ranged from 92% to 96%, whereas the combined diagnostic success rate for two samples collected at the same time was 100%. A clinically useful result only requires that one of the samples be amplifiable by PCR.

The practical implications of these results are significant. By collecting and analyzing two or more buccal samples at the same time from the same individual, it is possible to mitigate the effects of inhibitory substances in the sample and achieve a clinically useful result. This solves the reliability issue that has prevented saliva and buccal samples from being routinely used for amplification without purification.

Example 8

Cap Holder Device and Swabbing Procedure

To facilitate the use of the cap of a Spartan DX-12 tube to collect a buccal sample, one may construct an exemplary cap holder device using the following parts, shown in FIGS. 5 and 6:

One (1) Spartan DX-12 tube cap (Part #01004156), cap 501 in FIG. 5.

Three (3) 4 mm×150 mm drinking straws (Touch Industries, Part #92-004). One straw, straw 502, cut to 118 mm in length with a linear cut extending along the entire length of the straw. One straw, straw 503, cut to 129 mm in length with a linear cut extending along the entire length of the straw. One straw, straw 504, cut to 137 mm in length with a linear cut extending 10 mm inward from one extremity of the straw.

One (1) 4 mm×150 mm drinking straw (Touch Industries, Part #92-782). This straw, straw 505, is cut to 75 mm in length with a linear cut extending along the entire length of the straw. Straw 505 is used to make a cover for the Spartan DX-12 tube cap 505 and may have a closed end in accordance with various embodiments of the present invention.

The assembly process is as follows:

Insert cap 501 into the end of straw 504 in the orientation shown in FIG. 5. Cap 501 should be inserted into the portion of straw 504 with a linear cut extending 10 mm inward from one extremity. After assembly, the reference edge of straw 504, edge 514, should be 0.5±0.2 mm from the reference surface of cap 501, surface 601, shown in FIG. 6.

Slide straw 502 over straw 504. After assembly, the reference edges of straw 502 and straw 504, edges 512 and 514 respectively, shown in FIG. 5, should be aligned.

Insert straw 503 into the open end of straw 504 straw 503 comes into contact with the reference surface of cap 501, surface 511, shown in FIG. 5. After assembly, the reference edges of straws 503 and 504, edges 513 and 515, should be aligned.

Insert cover straw 505 over straw 504 so that the midpoint of cover 505 is aligned with the exposed end of cap 501, as shown in FIG. 5.

Fold the portion of straw 504 extending past the protruding end of cap 501 over on itself so that it completely covers cap 501.

In this way, a swab has been manufactured out of a Spartan DX-12 tube cap and the drinking straws. While members 501-505 are described as straws, these members may be composed of other tubular structures in accordance with various embodiments of the present invention. An exemplary swabbing procedure for using the manufactured swab is as follows:

1) Have the subject rinse his or her mouth with water. The subject may swallow or spit the rinse water.
2) Take one manufactured swab and one standard Spartan DX-12 reaction tube which has been pre-filled with nucleic acid amplification reagents and capped. Remove the cap from the Spartan DX-12 reaction tube and discard the cap.
3) Remove the cover (FIG. 5, Item "E") from the swab and discard.
4) Swab the inside of the subject's cheek by holding the shaft of the swab and rubbing the cap from the swab against the cheek up and down three times.
5) Insert the swab into the Spartan DX-12 reaction tube so that the cap from the swab seals the tube. Place your thumb on the end of the swab to ensure that there is sufficient pressure to completely seat the cap.
6) While holding the swab vertically with the tube pointed downward at an angle of approximately 30 degrees, gently tap the tube three (3) times to mix the reagents.
7) Insert the sealed tube into the Spartan DX-12 instrument and discard the shaft of the swab.

Example 9

Higher PCR Success Rate Using Dual HPLC Purified Probes and Cap Holder Device

Subjects whose CYP450 2C19 *1 and *2 genotypes had been determined previously were tested using three methods.

In the first method, PCR master mix was freshly mixed; aliquoted into Spartan DX-12 tubes; capped with Spartan DX-12 tube caps; and left at room temperature for 10 min. In parallel, 24 individuals swiped the inside of their cheek a total of six times (one swipe up, one swipe down, repeated three times) using a separate Spartan DX-12 tube cap. Subjects were asked not to eat or drink anything but water for 5 min prior to sample collection. Subjects were asked to rinse their mouths with water prior to sample collection. The cap with the buccal sample was then inserted into the tube containing PCR master mix, and the tube was tapped gently to ensure contact of the liquid with the part of the cap containing the sample. The capped tube with buccal sample was inserted into a Spartan DX-12 instrument 10 min after mixing the sample.

PCR primers were designed to amplify a 91 base pair amplicon from the human CYP 2C19 gene. The forward primer sequence was 5'-TgCAATAATTTTCCCACTAT-CATTg-3' (SEQ ID NO:1) and the reverse primer sequence was 5'-CCAAAATATCACTTTCCATAAAAgCA-3' (SEQ ID NO:2). Primers were manufactured by Integrated DNA Technologies. The TaqMan probe sequence for the wild-type gene was ttatttccc[g]ggaacc (SEQ ID NO:7). The probe was labeled at the 5' end with FAM and at the 3' end with Black Hole Quencher-1 plus (BHQ1plus). The brackets indicate the location of the wild-type single nucleotide polymorphism (SNP). The TaqMan probe sequence for the mutant gene was ttatttccc[a]ggaacc (SEQ ID NO:8) The probe was labeled at the 5' end with CalFluor 610 (CF610) and at the 3' end with Black Hole Quencher-2 (BHQ2). The brackets indicate the location of the mutant SNP. Probes were manufactured by Biosearch Technologies. All the individuals are expected to be successful for PCR and generate a fluorescent signal for the FAM probe because all individuals tested were known to carry at least one copy of the wild-type target allele; thus, the reaction contains an internal positive control.

The PCR master mix contained final concentrations of the following components:
PCR buffer (without Magnesium chloride) (Biotools): 1×
Magnesium chloride (Biotools): 2.5 mM
dNTPs (Invitrogen, Cat. No. 10297-018): 0.125 mM
Forward primer: 0.5 µM
Reverse primer: 0.5 µM
FAM probe: 0.1 µM
CalFluor 610 probe: 0.6 µM
DNA polymerase (Biotools): 1 Unit The PCR reaction volume was 20 µl. PCR was performed using the Spartan DX-12 instrument (Spartan Bioscience).

The PCR program had the following steps:
1) Initial denaturation: 95° C. for 10 min for 1 cycle
2) Cycling denaturation: 95° C. for 5 sec for 50 cycles
3) Cycling hybridization/extension: 50° C. for 10 sec for 50 cycles Endpoint fluorescence (EPF) was calculated for each sample by subtracting the fluorescence value at the first cycle from the fluorescence value at the last cycle. A test result was called as successful if the EPF for the FAM channel was greater than 9,800 arbitrary units. A test result was called as unsuccessful if the EPF for the FAM channel was less than or equal to 9,800 arbitrary units. Overall PCR success rate was calculated as total number of successful results divided by total number of results.

The same materials and methods were used in the second method, with the following exceptions: (1) both probes were dual HPLC purified; (2) the final concentrations of the FAM probe and CF610 probe were 0.2 µM and 0.4 µM, respectively; and (3) the temperature for cycling hybridization/extension was 55° C.

The third method only differed from the second method in that the cap holder device and swabbing method described in Example 8 were used to collect the buccal sample from subjects.

The overall PCR success rates for the three methods were 91.7 percent for the first method (24 subjects) 95.8 percent for the second method (24 subjects), and 97.9 percent for the third method (48 subjects).

Based on these results, PCR success rate may be improved by using dual HPLC purified probes.

The results in this example also indicate that PCR success rate may be improved by using the cap holder device of Example 8 for the Spartan DX-12 tube cap to collect a concentration range of buccal material that is compatible with direct amplification without purification. The increase in PCR success rate was found to be additive when combined with the use of dual HPLC purified probes.

Example 10

Direct Amplification without Purification from Non-Buccal Human Samples

Samples were collected from various body parts of one individual whose CYP450 2C19 *1 and *2 genotypes had been determined previously. The samples were collected by rubbing a cap from the Spartan DX-12 tube on the body part. Four samples each were collected from the palm, armpit, inside the folds of the pinna of the ear, and inside the nasal cavity. Prior to sample collection from the palm, the individual had been clenching his fist and his palm was sweaty.

Within 1 min after sample collection, the cap was inserted into a tube containing PCR master mix, and the tube was tapped gently to ensure contact of the liquid with the part of the cap containing the sample. The capped tube with sample was inserted into a Spartan DX-12 instrument 10 min after mixing the sample.

PCR primers were designed to amplify a 91 base pair amplicon from the human CYP 2C19 gene. The forward primer sequence was 5'-TgCAATAATTTTCCCACTAT-CATTg-3' (SEQ ID NO:1) and the reverse primers sequence was 5'-CCAAAATATCACTTTCCATAAAAgCA-3' (SEQ ID NO:2). Primers were manufactured by Integrated DNA Technologies. Both primers were HPLC purified. The Taq-Man probe sequence for the wild-type gene was ttatttccc[g]ggaacc (SEQ ID NO:7). The probe was labeled at the 5' end with FAM and at the 3' end with Black Hole Quencher-1 plus (BHQ1plus). The brackets indicate the location of the wild-type single nucleotide polymorphism (SNP). The TaqMan probe sequence for the mutant gene was ttatttccc[a]ggaacc (SEQ ID NO:8). The probe was labeled at the 5' end with CalFluor 610(CF610) and at the 3' end with Black Hole Quencher-2 plus (BHQ2plus). The brackets indicate the location of the mutant SNP. Probes were manufactured by Biosearch Technologies. Both probes were dual HPLC purified.

The PCR master mix contained final concentrations of the following components:
  GoTaq master mix (containing final 1.5 mM magnesium chloride) (Promega): 1×
  Additional magnesium chloride (Biotools): 1.5 mM
  Forward primer: 0.5 µM
  Reverse primer: 0.5 µM
  FAM probe: 0.2 µM
  CalFluor 610 probe: 0.4 µM
  GoTaq DNA polymerase (Promega): 1 Unit
The PCR reaction volume was 21 µl. PCR was performed using the Spartan DX-12 instrument (Spartan Bioscience).

The PCR program had the following steps:
  1) Initial denaturation: 95° C. for 15 min for 1 cycle
  2) Cycling denaturation: 95° C. for 5 sec for 50 cycles
  3) Cycling hybridization/extension: 58° C. for 10 sec for 50 cycles Results were analyzed using Microsoft™ Excel™. Endpoint fluorescence (EPF) was calculated for each sample by subtracting the fluorescence value at the first cycle from the fluorescence value at the last cycle. A test result was called as unsuccessful if the EPF was smaller than or equal to the average plus 2 times the standard deviation of EPF of multiple negative controls containing no nucleic acid template.

Results showed that the correct genotype was obtained in 3 out of 4 palm samples, 1 out of 4 armpit samples, 2 out of 4 ear samples, and 3 out of 4 nose samples. These results indicate that non-buccal samples may also be used for direct nucleic acid amplification without purification.

Example 11

Direct Amplification without Purification from Non-Buccal Non-Human Samples

Whole blood was collected from raw pork liver and DNA was purified using the Arrow DNA Purification Robot (Nor-Diag, Oslo, Norway) and the Arrow Blood-200 kit, according to the manufacturer's instructions. Purified DNA was quantified using the NANODROP spectrophotometer (Thermo Scientific). In parallel, a sample was collected from a fresh pork chop by rubbing a cap from the Spartan DX-12 tube on the raw meat. Immediately after sample collection, the cap was inserted into a tube containing PCR master mix, and the tube was tapped gently to ensure contact of the liquid with the part of the cap containing the sample. The capped tube with sample was inserted into a Spartan DX-12 instrument after mixing the sample.

PCR primers were designed to amplify a 130 base pair amplicon from the porcine Cytochrome B gene (Tanabe S et al. (2007). A quantitative PCR detection method for pork, chicken, beef, mutton, and horseflesh in foods. Bioscience, Biotechnology, and Biochemistry. 71(12): 3131-3135.). The forward primer sequence was 5'-gttgcaaatcctaacaggcctg-3' (SEQ ID NO:5) and the reverse primer sequence was 5'-cgtttgcatgtagatagcgaataac-3' (SEQ ID NO:6). Primers were manufactured by Integrated DNA Technologies.

The PCR master mix contained final concentrations of the following components:
  PCR Buffer (Biotools): 1×
  dNTPs (Invitrogen): 0.125 mM
  Magnesium chloride (Biotools): 2.5 mM
  Forward primer: 0.5 µM
  Reverse primer: 0.5 µM
  SYBR Green (Invitrogen): 0.5×
  Taq DNA polymerase (Biotools): 1 Unit
For the DNA purified from blood, the final amount of DNA in the reaction mixture was 21 ng. The PCR reaction volume was 20 µl. PCR was performed using the Spartan DX-12 instrument (Spartan Bioscience).

The PCR program had the following steps:
  1) Initial denaturation: 95° C. for 10 min for 1 cycle
  2) Cycling denaturation: 95° C. for 30 sec for 50 cycles
  3) Cycling hybridization/extension: 60° C. for 60 sec for 50 cycles Amplicons were analyzed using gel electrophoresis. PCR generated amplicons of the expected size for DNA purified from blood and samples collected by rubbing the Spartan DX-12 cap on the raw pork chop.

This experiment demonstrates that swabs from non-human samples may be used for direct amplification without purification according to the method described in this invention. Other suitable non-human samples may include and are not limited to fish, shellfish, beef, chicken, and lamb.

Other Embodiments

Other embodiments will be apparent to those skilled in the art from a consideration of the specification or practice of the invention disclosed herein. It is intended that the specification and examples be considered as exemplary only, with the true scope of the invention being indicated by the following claims. The entire contents of any reference that is referred to herein are hereby incorporated by reference.

In accordance with 37 CFR 1.52(e)(5), a Sequence Listing in the form of a text file (entitled "Seq_Listing_2009379-0028_ST25 .txt," created on Sep. 24, 2012 and 1.5 Kb) is incorporated herein by reference in its entirety.

What is claimed is:

1. A method comprising steps of:
obtaining a swab sample comprising nucleic acid from a source;
contacting the swab sample with a nucleic acid amplification reagent in a reaction vessel, wherein the swab sample is directly contacted with the nucleic acid amplification reagent without any intervening steps, wherein the nucleic acid amplification reagent comprises:
   a) a DNA polymerase at a concentration of at least 1.0 U/reaction;
   b) a primer at a concentration of at least 0.2 µM;
   c) a probe at a concentration of at least 0.2 µM; and
performing a nucleic acid amplification reaction on the swab sample.

2. The method of claim 1, wherein the DNA polymerase is at a concentration of at least 2.0 U/reaction.

3. The method of claim 1, further comprising the step of, determining whether an amplification product was produced as a result of the nucleic acid amplification reaction.

4. The method of claim 1, wherein the nucleic acid amplification reaction is performed within 120 minutes of contacting the swab sample with the nucleic acid amplification reagents.

5. The method of claim 1, wherein the nucleic acid amplification reaction is performed within 60 minutes of contacting the swab sample with the nucleic acid amplification reagents.

6. The method of claim 1, wherein the nucleic acid amplification reaction is performed within 30 minutes of contacting the swab sample with the nucleic acid amplification reagents.

7. The method of claim 1, wherein the nucleic acid amplification reaction is performed within 15 minutes of contacting the swab sample with the nucleic acid amplification reagents.

8. The method of claim 1, wherein the nucleic acid amplification reaction is performed within 10 minutes of contacting the swab sample with the nucleic acid amplification reagents.

9. The method of claim 1, wherein the nucleic acid amplification reaction is performed within 5 minutes of contacting the swab sample with the nucleic acid amplification reagents.

10. The method of claim 1, wherein the nucleic acid amplification reaction is performed within 1 minute of contacting the swab sample with the nucleic acid amplification reagents.

11. The method of claim 1, wherein the step of performing a nucleic acid amplification reaction on the swab sample comprises an initial heat denaturation step of 15 minutes or less.

12. The method of claim 1, wherein the step of performing a nucleic acid amplification reaction on the swab sample comprises an initial heat denaturation step of 5 minutes or less.

13. The method of claim 1, wherein the step of performing a nucleic acid amplification reaction on the swab sample comprises an initial heat denaturation step of 3 minutes or less.

14. The method of claim 1, wherein the step of performing a nucleic acid amplification reaction on the swab sample comprises an initial heat denaturation step of 1 minute or less.

15. The method of claim 1, wherein the step of obtaining comprises collecting the swab sample.

16. The method of claim 15, wherein the swab sample is collected from a mammal.

17. The method of claim 16, wherein the mammal is a human.

18. The method of claim 16, wherein the swab sample is collected from an open body cavity.

19. The method of claim 16, wherein the swab sample is collected from a body surface.

20. The method of claim 16, wherein the swab sample is a buccal sample.

21. The method of claim 16, wherein the swab sample is collected from the group consisting of the palm of a hand, inside the folds of the pinna of an ear, an armpit, inside a nasal cavity and combinations thereof.

22. The method of claim 15, wherein the swab sample is collected from a foodstuff.

23. The method of claim 22, wherein the foodstuff is raw.

24. The method of claim 22, wherein the foodstuff is a fruit, a vegetable, a meat, a fish, or a shellfish.

25. The method of claim 24, wherein the meat is pork, beef, chicken or lamb.

26. The method of claim 15, wherein the reaction vessel comprises a removable cap and the cap is used to collect the swab sample.

27. The method of claim 26, wherein a means for holding the cap is used when collecting the swab sample.

28. The method of claim 26, wherein the cap is contacted with the inside of a cheek.

29. The method of claim 26, wherein the cap is contacted with a tongue.

30. The method of claim 26, wherein the cap is contacted with a body region selected from the group consisting of the palm of a hand, the inside of the folds of the pinna of an ear, an armpit, the inside of a nasal cavity and combinations thereof.

31. The method of claim 26, wherein the cap is contacted with a foodstuff.

32. The method of claim 31, wherein the foodstuff is raw.

33. The method of claim 31, wherein the foodstuff is selected from the group consisting of a fruit, a vegetable, a meat, a fish, a shellfish and combinations thereof.

34. The method of claim 33, wherein the meat is pork, beef, chicken or lamb.

35. The method of claim 15, wherein the swab sample is collected from a source and the method is repeated with at least one additional swab sample from the same source.

36. The method of claim 1, wherein the nucleic acid amplification reaction is performed in a reaction vessel having a removable cap and the cap is used to collect the swab sample.

37. The method of claim 36, wherein the reaction vessel comprises the nucleic acid amplification reagent and the cap is used to seal the reaction vessel after the swab sample has been collected.

38. The method of claim 36, wherein a means for holding the cap is used when collecting the swab sample.

39. The method according to claim 1, wherein contacting the nucleic acid amplification reagent with the swab sample comprises agitating the container.

40. The method according to claim 1, wherein the nucleic acid amplification reagent is not modified to resist inhibitors.

41. A method comprising the steps of:
(a) obtaining a swab sample comprising nucleic acid from a source; and
(b) contacting the swab sample with a nucleic acid amplification reagent in a reaction vessel without any intervening steps; and
(c) performing a nucleic acid amplification reaction on the swab sample, wherein the nucleic acid amplification reaction is performed within 60 minutes of contacting the swab sample with the nucleic acid amplification reagents.

42. The method of claim 2, wherein the primer is at a concentration of at least 0.3 µM; and the probe is at a concentration of at least 0.4 µM.

43. The method of claim 1, wherein the primer is at a concentration of at least 0.5 µM; and the probe is at a concentration of at least 0.7 µM.

44. The method of claim 2, wherein the primer is at a concentration of at least 0.3 µM; and the probe is at a concentration of at least 0.4 µM.

45. The method of claim 2, wherein the primer is at a concentration of at least 0.5 µM; and the probe is at a concentration of at least 0.7 µM.

46. The method of claim 38, wherein the cap is a solid plug cap which comprises:
a) a tip that is capable of protruding into and mating with the reaction vessel; and
b) an end opposing the tip that is capable of mating with the means for holding the cap, wherein the solid cap is arranged and constructed to sealingly nest within an upper cylindrical portion of the reaction vessel and partially within a lower frustoconical portion of the reaction vessel.

\* \* \* \* \*

UNITED STATES PATENT AND TRADEMARK OFFICE
CERTIFICATE OF CORRECTION

PATENT NO. : 8,735,104 B2
APPLICATION NO. : 13/637006
DATED : May 27, 2014
INVENTOR(S) : Chris Harder et al.

Page 1 of 1

It is certified that error appears in the above-identified patent and that said Letters Patent is hereby corrected as shown below:

In the Claims

In Column 31, line 17, under Claim "42", please delete "claim 2" and replace with "claim 1".

Signed and Sealed this
Sixth Day of January, 2015

Michelle K. Lee
*Deputy Director of the United States Patent and Trademark Office*